US008332013B2

(12) United States Patent
Strommer

(10) Patent No.: US 8,332,013 B2
(45) Date of Patent: *Dec. 11, 2012

(54) SYSTEM AND METHOD FOR DELIVERING A STENT TO A SELECTED POSITION WITHIN A LUMEN

(75) Inventor: Gera Strommer, Haifa (IL)

(73) Assignee: MediGuide, Ltd., Haifa (IL)

( * ) Notice: Subject to any disclaimer, the term of this patent is extended or adjusted under 35 U.S.C. 154(b) by 0 days.

This patent is subject to a terminal disclaimer.

(21) Appl. No.: 12/841,671

(22) Filed: Jul. 22, 2010

(65) Prior Publication Data

US 2010/0331950 A1 Dec. 30, 2010

Related U.S. Application Data

(63) Continuation of application No. 10/938,395, filed on Sep. 9, 2004, now Pat. No. 7,778,688, which is a continuation-in-part of application No. 09/949,160, filed on Sep. 7, 2001, now Pat. No. 7,343,195, which is a continuation-in-part of application No. 09/782,528, filed on Feb. 13, 2001, now Pat. No. 7,386,339, which is a continuation-in-part of application No. 09/314,474, filed on May 18, 1999, now Pat. No. 6,233,476.

(51) Int. Cl.
*A61B 5/05* (2006.01)

(52) U.S. Cl. ........ 600/424; 600/407; 600/415; 600/429; 600/434; 600/439; 382/128; 604/521

(58) Field of Classification Search .................. 600/424, 600/434, 407, 415; 382/128; 604/521
See application file for complete search history.

(56) References Cited

U.S. PATENT DOCUMENTS 3,974,826 A 8/1976 Eggleton et al.
(Continued)

FOREIGN PATENT DOCUMENTS

EP 0894473 2/1999
(Continued)

OTHER PUBLICATIONS

Panza, Julio A., "Real-time three-dimensional echocardiography: An overview", *The International Journal of Cardiovascular Imaging* 17:227-235, 2001.

*Primary Examiner* — Tse Chen
*Assistant Examiner* — Baisakhi Roy
(74) *Attorney, Agent, or Firm* — Dykema Gossett PLLC

(57) ABSTRACT

Method for delivering a stent coupled with a catheter, to a selected position within a lumen of the body of a patient, the method includes the procedures of: selecting a single image of the lumen, among a plurality of images of an image sequence of the lumen, receiving a position input associated with the selected image and respective of the selected position, the position input is defined in a coordinate system respective of a medical positioning system (MPS), detecting the current position of the stent in the coordinate system, according to position data acquired by an MPS sensor attached to the catheter in the vicinity of the stent, superimposing on at least one maneuvering associated image of the lumen, at least one stent representation respective of the current position, and at least one marking representation respective of the position input, according to a real-time organ timing signal of an inspected organ of the body, maneuvering the catheter through the lumen, toward the selected position, according to the current position relative to the position input, and producing an output when the current position substantially matches the selected position.

19 Claims, 22 Drawing Sheets

U.S. PATENT DOCUMENTS

| | | | |
|---|---|---|---|
| 3,990,296 A | 11/1976 | Erikson | |
| 4,737,794 A | 4/1988 | Jones | |
| 5,016,642 A | 5/1991 | Dukes et al. | |
| 5,152,290 A | 10/1992 | Freeland | |
| 5,159,931 A | 11/1992 | Pini | |
| 5,360,008 A | 11/1994 | Campbell | |
| 5,398,691 A | 3/1995 | Martin et al. | |
| 5,445,150 A | 8/1995 | Dumoulin et al. | |
| 5,453,686 A | 9/1995 | Anderson | |
| 5,529,070 A | 6/1996 | Augustine et al. | |
| 5,577,502 A | 11/1996 | Darrow et al. | |
| 5,588,432 A | 12/1996 | Crowley | |
| 5,622,174 A | 4/1997 | Yamazaki | |
| 5,669,385 A | 9/1997 | Pesque et al. | |
| 5,690,113 A | 11/1997 | Sliwa, Jr. et al. | |
| 5,724,982 A * | 3/1998 | Schnurer et al. | 600/505 |
| 5,730,129 A | 3/1998 | Darrow et al. | |
| 5,740,808 A | 4/1998 | Panescu et al. | |
| 5,744,953 A | 4/1998 | Hansen | |
| 5,787,889 A | 8/1998 | Edwards et al. | |
| 5,806,521 A | 9/1998 | Morimoto et al. | |
| 5,810,008 A | 9/1998 | Dekel et al. | |
| 5,830,145 A | 11/1998 | Tenhoff | |
| 5,830,222 A | 11/1998 | Makower | |
| 5,846,200 A | 12/1998 | Schwartz | |
| 5,899,860 A | 5/1999 | Pfeiffer et al. | |
| 5,906,578 A | 5/1999 | Rajan et al. | |
| 5,913,820 A | 6/1999 | Bladen et al. | |
| 5,924,989 A | 7/1999 | Polz | |
| 5,928,248 A | 7/1999 | Acker | |
| 5,935,075 A | 8/1999 | Casscells | |
| 5,938,606 A | 8/1999 | Bonnefous | |
| 5,949,491 A | 9/1999 | Callahan et al. | |
| 5,955,879 A | 9/1999 | Durdle et al. | |
| 5,957,844 A | 9/1999 | Dekel et al. | |
| 5,967,980 A | 10/1999 | Ferre et al. | |
| 5,976,088 A | 11/1999 | Urbano et al. | |
| 5,993,390 A | 11/1999 | Savord et al. | |
| 5,994,690 A | 11/1999 | Kulkarni et al. | |
| 6,006,126 A | 12/1999 | Cosman | |
| 6,030,343 A | 2/2000 | Chechersky et al. | |
| 6,035,856 A | 3/2000 | LaFontaine et al. | |
| 6,047,080 A | 4/2000 | Chen et al. | |
| 6,134,003 A | 10/2000 | Tearney et al. | |
| 6,148,095 A | 11/2000 | Prause et al. | |
| 6,169,917 B1 | 1/2001 | Masotti et al. | |
| 6,175,669 B1 | 1/2001 | Colston et al. | |
| 6,216,029 B1 | 4/2001 | Paltieli | |
| 6,228,028 B1 | 5/2001 | Klein et al. | |
| 6,233,476 B1 | 5/2001 | Strommer et al. | |
| 6,246,898 B1 | 6/2001 | Vesely et al. | |
| 6,275,724 B1 | 8/2001 | Dickinson et al. | |
| 6,317,621 B1 | 11/2001 | Graumann et al. | |
| 6,381,350 B1 * | 4/2002 | Klingensmith et al. | 382/128 |
| 6,385,476 B1 | 5/2002 | Osadchy et al. | |
| 6,390,982 B1 | 5/2002 | Bova et al. | |
| 6,405,072 B1 | 6/2002 | Cosman | |
| 6,416,476 B1 | 7/2002 | Ogasawara et al. | |
| 6,470,207 B1 | 10/2002 | Simon et al. | |
| 6,498,944 B1 | 12/2002 | Ben-Haim et al. | |
| 6,501,981 B1 | 12/2002 | Schweikard et al. | |
| 6,546,271 B1 | 4/2003 | Reisfeld | |
| 6,556,695 B1 | 4/2003 | Packer et al. | |
| 6,733,458 B1 | 5/2004 | Steins et al. | |
| 6,788,967 B2 | 9/2004 | Ben-Haim et al. | |
| 7,156,655 B2 * | 1/2007 | Sachdeva et al. | 433/24 |
| 7,197,354 B2 | 3/2007 | Sobe | |
| 7,263,397 B2 | 8/2007 | Hauck et al. | |
| 7,343,195 B2 | 3/2008 | Strommer et al. | |
| 7,386,339 B2 | 6/2008 | Strommer et al. | |
| 7,778,688 B2 * | 8/2010 | Strommer | 600/424 |
| 2001/0031919 A1 | 10/2001 | Strommer et al. | |
| 2001/0044578 A1 | 11/2001 | Ben-Haim et al. | |
| 2002/0049375 A1 | 4/2002 | Strommer et al. | |
| 2002/0193686 A1 | 12/2002 | Gilboa | |
| 2003/0074011 A1 | 4/2003 | Gilboa et al. | |
| 2004/0034297 A1 | 2/2004 | Darrow et al. | |
| 2004/0138548 A1 | 7/2004 | Strommer et al. | |
| 2004/0215071 A1 | 10/2004 | Frank et al. | |
| 2005/0033149 A1 | 2/2005 | Strommer et al. | |
| 2005/0107688 A1 | 5/2005 | Strommer et al. | |
| 2005/0197557 A1 | 9/2005 | Strommer et al. | |
| 2006/0058647 A1 | 3/2006 | Strommer et al. | |
| 2006/0064006 A1 | 3/2006 | Strommer et al. | |
| 2006/0079745 A1 | 4/2006 | Viswanathan | |
| 2007/0287901 A1 | 12/2007 | Strommer et al. | |
| 2008/0175463 A1 | 7/2008 | Strommer et al. | |
| 2009/0182224 A1 | 7/2009 | Shmarak et al. | |
| 2010/0331950 A1 | 12/2010 | Strommer | |

FOREIGN PATENT DOCUMENTS

| | | |
|---|---|---|
| EP | 1088515 | 4/2001 |
| JP | 62032304 | 2/1987 |
| JP | 8500441 | 1/1996 |
| JP | 11110114 | 4/1999 |
| JP | 2001170027 | 6/2001 |
| JP | 2002200058 | 7/2002 |
| JP | 2007502187 | 2/2007 |
| WO | WO-96/05768 | 2/1996 |
| WO | WO-96/41119 | 12/1996 |
| WO | WO-97/29685 | 8/1997 |
| WO | WO-97/36143 | 10/1997 |
| WO | WO-97/29682 | 9/1999 |
| WO | WO-99/43253 | 9/1999 |
| WO | WO-00/10456 | 3/2000 |
| WO | WO-00/16684 | 3/2000 |
| WO | WO-02/064011 | 8/2002 |
| WO | WO-03/059167 | 7/2003 |
| WO | WO-01/62501 | 7/2004 |
| WO | WO-2004/060157 | 7/2004 |
| WO | WO-2005/039391 | 5/2005 |

* cited by examiner

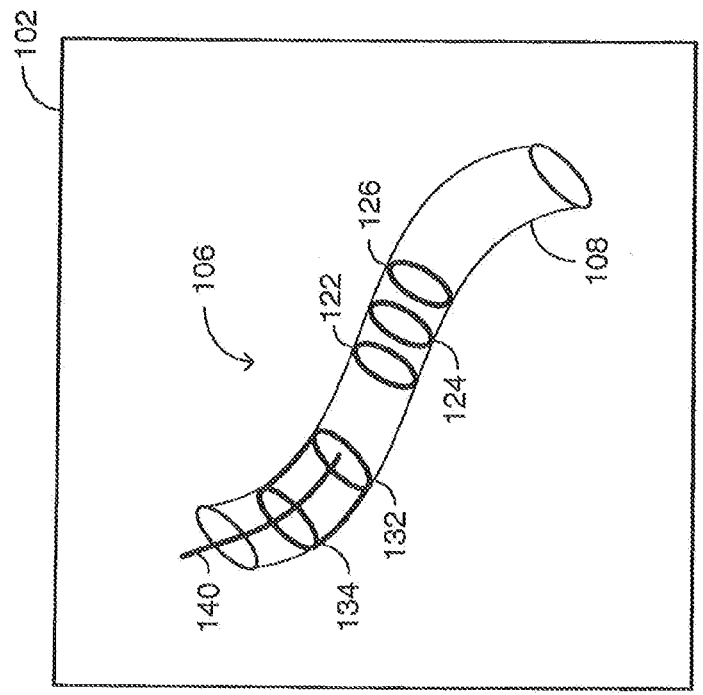
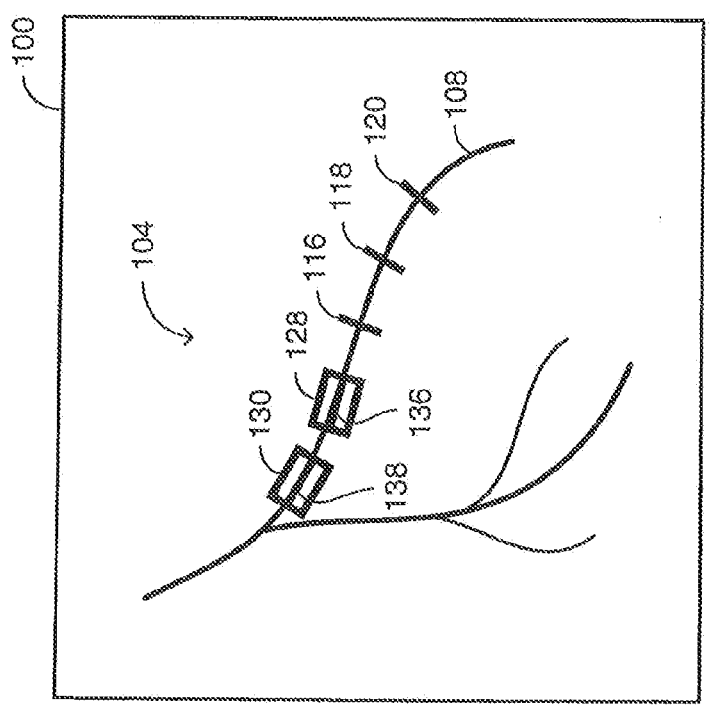
FIG. 2B
FIG. 2A

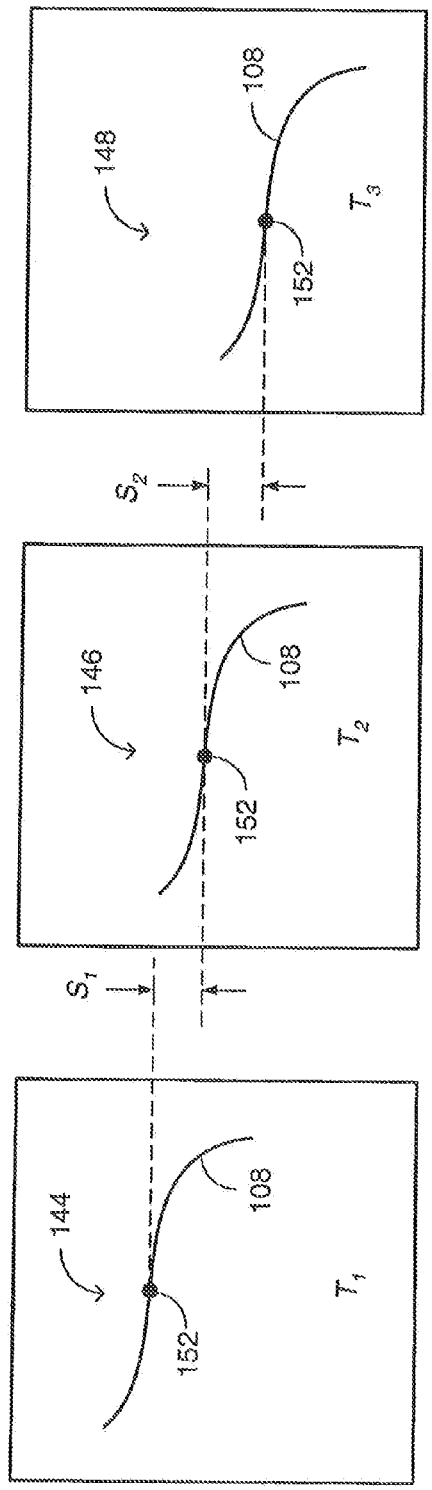
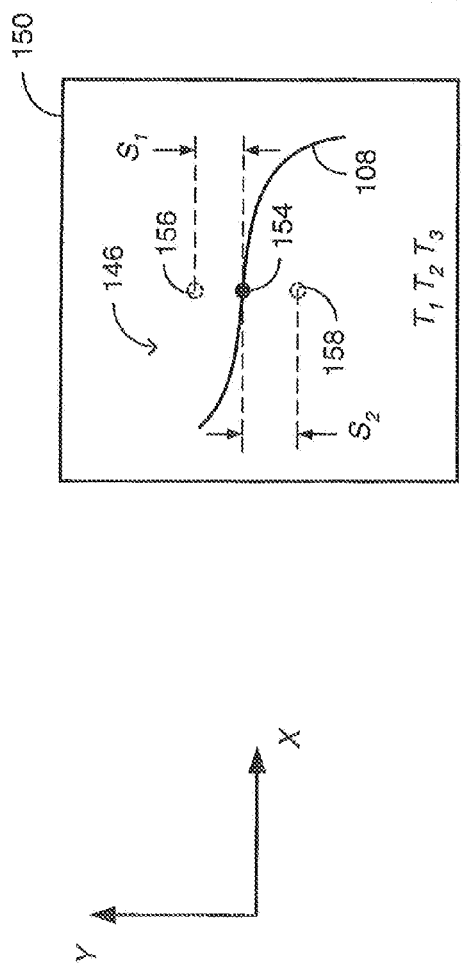
FIG. 4A
FIG. 4B
FIG. 4C
FIG. 4D

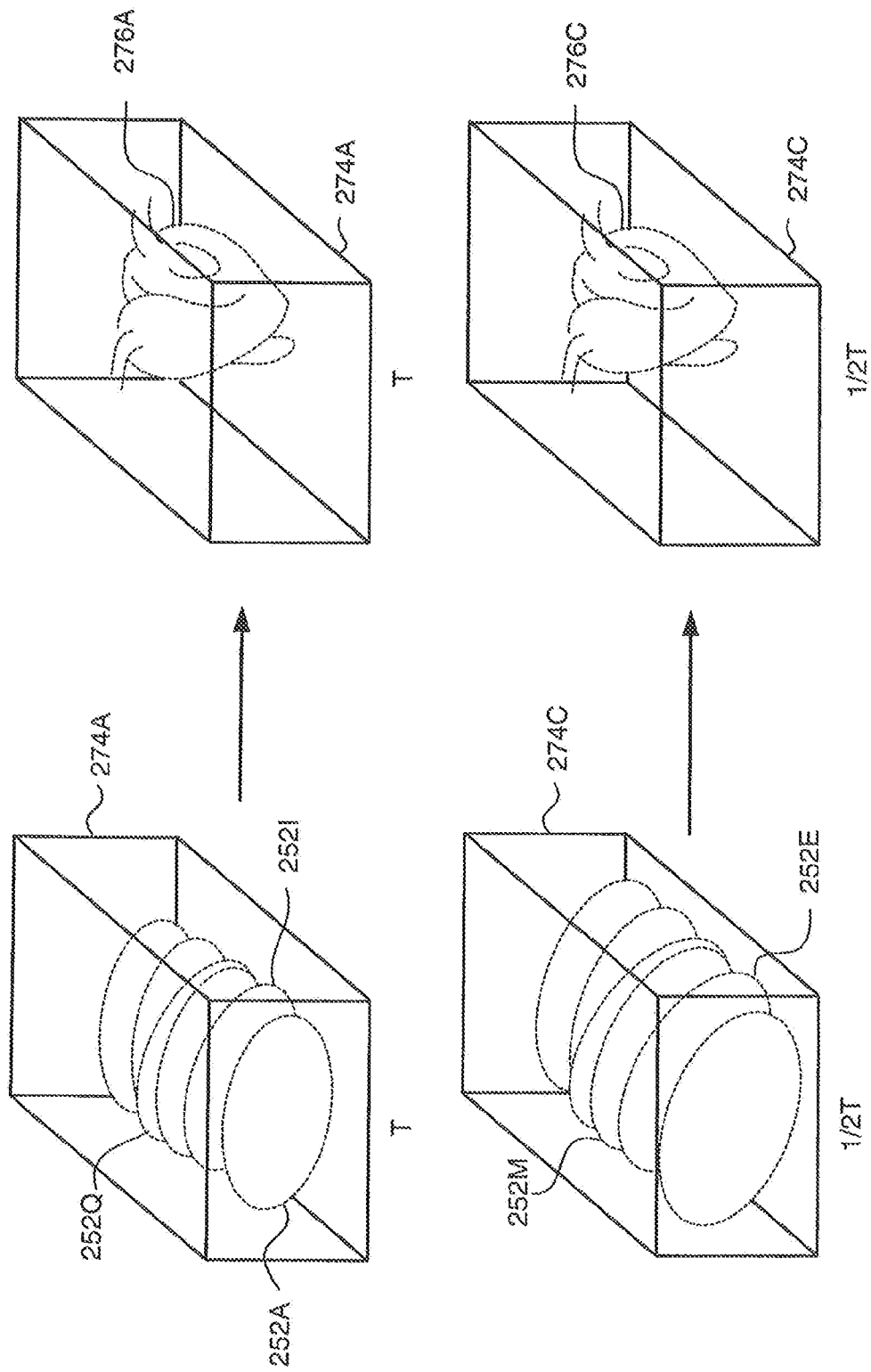

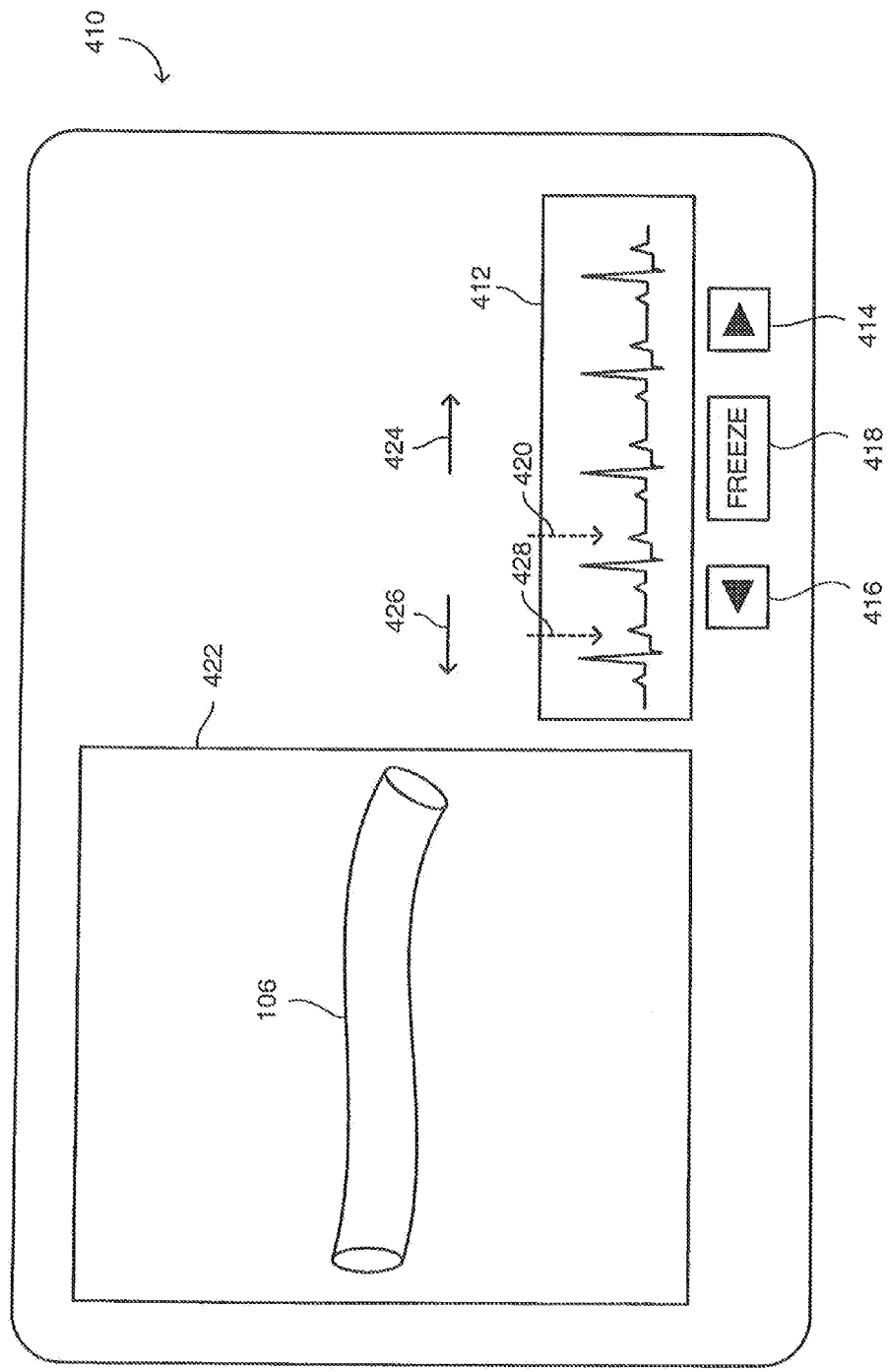

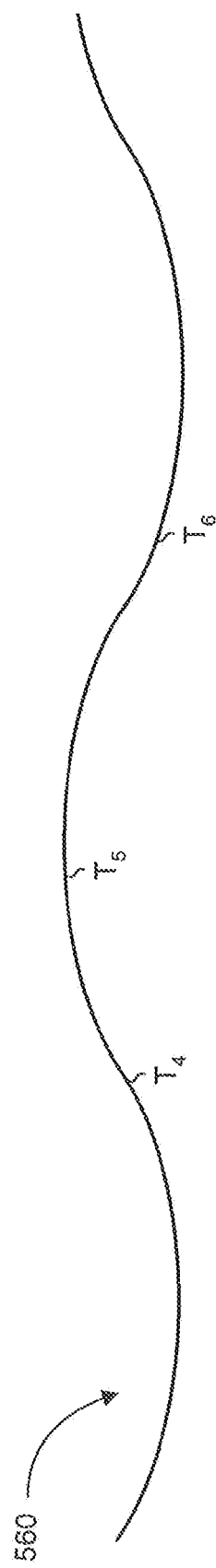

SYSTEM AND METHOD FOR DELIVERING A STENT TO A SELECTED POSITION WITHIN A LUMEN

CROSS-REFERENCE TO RELATED APPLICATIONS

This application is a continuation of U.S. application Ser. No. 10/938,395 filed on Sep. 9, 2004, now allowed, which is a continuation-in-part (CIP) of U.S. application Ser. No. 09/949,160, filed on Sep. 7, 2001, now U.S. Pat. No. 7,343, 195, which is a continuation-in-part (CIP) of U.S. application Ser. No. 09/782,528, filed on Feb. 13, 2001, now U.S. Pat. No. 7,386,339, which is a continuation-in-part (CIP) of U.S. application Ser. No. 09/314,474, filed on May 18, 1999, now U.S. Pat. No. 6,233,476. The entire disclosures of the above applications are hereby incorporated by reference herein.

FIELD OF THE DISCLOSED TECHNIQUE

The disclosed technique relates to medical operations in general, and to methods and systems for mounting a stent in the body of a patient, in particular.

BACKGROUND OF THE DISCLOSED TECHNIQUE

An occluded vessel in the body of a patient is cleared by severing the occluding matter (e.g., the intima of a blood vessel), for example by inflating a balloon (i.e., angioplasty), applying a cryogenic fluid, exposing the vessel to laser or an electric potential, and removing matter by a rotating blade (rotablator). This severing action initiates a healing process in the vessel, which causes production of new tissue cells, thereby once again constricting the passage through the vessel. The growth of tissue cells occurs over a period of a few months following the surgery. In order to keep the passageway open for a longer period of time, and prevent tissue cell to grow as a result of healing, a rigid thin wall tube whose wall is in form of wire mesh (i.e., stent) is mounted in the severed portion of the vessel, within the vessel.

Methods and systems for maneuvering the stent catheter to the desired location within the vessel, after severing the vessel are known in art. For example, a marker band is attached to the catheter close to the stent, thereby enabling the physician to navigate the catheter by viewing the marker band in a real-time X-ray image of the vessel. In another case, the physician can view a representation of the position and orientation of the stent on the real-time X-ray image, according to position and orientation data acquired by a medical positioning system (MPS) sensor, attached to the catheter close to the stent.

U.S. Pat. No. 5,928,248 issued to Acker and entitled "Guided Deployment of Stents", is directed to an apparatus for applying a stent in a tubular structure of a patient. The apparatus includes a catheter, a hub, a pressure control device, a balloon, a stent, a probe field transducer, a plurality of external field transducers, a field transmitting and receiving device, a computer, an input device and a cathode ray tube. The catheter includes a bore. The hub is affixed to a proximal end of the catheter. The balloon is mounted on a distal end of the catheter. The pressure control device is connected to the balloon through the hub and the bore. The stent is made of a shape memory alloy and is located on the balloon.

The probe field transducer is located within the catheter, at a distal end thereof. The external field transducers are located outside of the patient (e.g., connected to the patient-supporting bed). The field transmitting and receiving device is connected to the external field transducers, the probe field transducer and to the computer. The computer is connected to the cathode ray tube and to the input device.

A user calibrates the field transmitting and receiving device in an external field of reference, by employing the external field transducers. The field transmitting and receiving device together with the computer, determine the position and orientation of the probe field transducer in the external field of reference. The user views the position and orientation of a representation of the stent which is located within a tubular structure of the patient, on the cathode ray tube. When the user determines that the distal end is located at the desired location within the tubular structure, the user expands the stent by operating the pressure control device and inflating the balloon, thereby positioning the stent at the desired location.

U.S. Pat. No. 5,830,222 issued to Makower and entitled "Device, System and Method for Interstitial Transvascular Intervention", is directed to a method for gaining percutaneous access to a diseased vessel through an adjacent intact vessel. Using this method, it is possible to bypass the diseased vessel, such as a coronary artery, through the intact vessel, such as a cardiac vein. The diseased vessel may include an occlusion that restricts the flow. A guide-catheter is advanced through the vena cava into the coronary sinus, within the right atrium of the heart. A transvascular interstitial surgery (TVIS) guide catheter is inserted through the guide-catheter and advanced through the cardiac vein over a first guidewire, to a desired location adjacent the coronary artery.

The TVIS guide-catheter includes a balloon, a TVIS probe and either or both of active orientation detection means and passive orientation detection means. The TVIS probe is a rigid wire, antenna, light guide or energy guide capable of being inserted in tissue. The passive orientation detection means allow radiographic, fluoroscopic, magnetic or sonographic detection of position and orientation of the TVIS probe. The active orientation detection means is a transmitter. A second guidewire is inserted into the coronary artery adjacent the cardiac vein, wherein the second guidewire includes a small receiver to receive a signal emitted by the active orientation detection means. The second guidewire further includes a wire bundle which is capable to return the signal detected by the receiver, to an operator, thereby enabling the operator to determine the position and location of the TVIS probe.

When the orientation of the TVIS guide-catheter is assured, the balloon is inflated against the wall of the cardiac vein, in order to block the flow, stabilize the TVIS guide-catheter within the cardiac vein and dilate the passageway. The TVIS probe, is then advanced through the wall of the cardiac vein into the coronary artery, thereby bypassing the diseased section of the coronary artery.

US Patent Publication No. 20020049375 entitled "Method and Apparatus for Real Time Quantitative Three-Dimensional Image Reconstruction of a Moving Organ and Intra-Body Navigation", is directed to a system for displaying an image of a lumen of a patient into which a surgical catheter is inserted, while taking into account the movements of the lumen caused by the heart beats of the patient. The system includes the surgical catheter, an imaging catheter, an imaging system, a medical positioning system (MPS), a transmitter, a body MPS sensor, a processor, a plurality of electrocardiogram (ECG) electrodes, an ECG monitor, a database, and a display. The surgical catheter includes a catheter MPS sensor located at a tip thereof. The imaging catheter includes an imaging MPS sensor and an image detector, both located at a tip of the imaging catheter.

The ECG electrodes are attached to the body of the patient and to the ECG monitor. The body MPS sensor is attached to the body of the patient and to the MPS. The processor is coupled with the imaging system, the MPS, the ECG monitor, the database and with the display. The MPS is coupled with the transmitter. During the scanning procedure the MPS is coupled with the imaging MPS sensor. During the surgical procedure the MPS is coupled with the catheter MPS sensor. The imaging system is coupled with the image detector. The imaging MPS sensor and the catheter MPS sensor send a signal respective of the position and orientation of the tip of the imaging catheter and the surgical catheter, respectively, to the MPS.

During the scanning procedure, an operator inserts the imaging catheter into the lumen and advances it therein, while the image detector scans the inner wall of the lumen and transmits detected two-dimensional images to the imaging system. The processor reconstructs a plurality of three-dimensional images according to the two-dimensional images and according to the coordinates of the tip of the imaging catheter determined by the MPS, while the processor associates each three-dimensional image with a respective activity state of the heart of the patient.

During the surgical procedure, the operator inserts the surgical catheter into the lumen and the catheter MPS sensor sends a location signal respective of the position and orientation of the tip of the surgical catheter to the MPS. As the operator moves the surgical catheter within the lumen, the processor determines a sequence of three-dimensional images of the lumen by retrieving data from the database, and according to the current position and orientation of the tip of the surgical catheter and the current activity state of the heart of the patient. The display displays the three-dimensional images in sequence, according to a video signal received from the processor.

U.S. Pat. No. 6,035,856 issued to LaFontaine et al., and entitled "Percutaneous Bypass with Branching Vessel", is directed to a method for performing a bypass on a first occlusion of a branching vessel of the aorta. A coronary artery which includes the first occlusion, and a branching vessel branch out of the aorta. A standard guide-catheter is advanced through the aorta up to the ostium of the branching vessel. An occlusion forming device is advanced through the guide-catheter into the branching vessel, to produce a second occlusion in the branching vessel. The occlusion device includes an elongate portion and a heated balloon.

The occlusion forming device is removed from the aorta through the guide-catheter and a cutting device is advanced through the guide-catheter proximal to the second occlusion. The cutting device includes an elongate member, a steerable guidewire, a proximal occlusion balloon, a distal balloon, a stent, a cutting blade, a first piece of magnetic material and a transmitter. The cutting blade is located distal to the distal balloon, the first piece of the magnetic material is located between the cutting blade and the distal balloon and the transmitter is located within the distal balloon. The distal balloon is located within the stent. The transmitter emits radio frequency signals.

The wall of the branching vessel is cut by employing the cutting blade. The distal balloon is kept in the expanded position, in order to occlude the branching vessel after the branching vessel has been cut. The severed end of the branching vessel is steered toward a region of the coronary artery distal to the first occlusion, by maneuvering the steerable guidewire or by manipulating the first piece of the magnetic material by a second piece of magnetic material, wherein the second piece of magnetic material is located outside the body of the patient.

The true position and the relative position of the transmitter and thus the position of the severed end of the branching vessel, is determined by employing a triangulation and coordinate mapping system. The triangulation and coordinate mapping system includes three reference electrodes which are located outside the body of the patient. Two of the reference electrodes are located on opposite sides of the heart and the third is located on the back. The three reference electrodes are used to triangulate on the transmitter.

When the severed end of the branching vessel is properly positioned, an aperture is formed in the coronary artery distal to the first occlusion, by employing the cutting blade. The severed end of the branching vessel is inserted into the coronary artery through the aperture and the stent is expanded by inflating the distal balloon, thereby attaching the severed end of the branching vessel to the lumen of the coronary artery.

SUMMARY OF THE DISCLOSED TECHNIQUE

It is an object of the disclosed technique to provide a novel method and system for navigating, delivering and deploying a stent within a tubular organ.

In accordance with the disclosed technique, there is thus provided a method for delivering a stent coupled with a catheter, to a selected position within a lumen of the body of a patient. The method includes the procedures of:

selecting a single image of the lumen, among a plurality of images of an image sequence of the lumen.

receiving a position input associated with the selected image and respective of the selected position. The position input is defined in a coordinate system respective of a medical positioning system (MPS).

detecting the current position of the stent in the coordinate system, according to position data acquired by an MPS sensor attached to the catheter in the vicinity of the stent.

superimposing on at least one maneuvering associated image of the lumen, at least one stent representation respective of the current position, and at least one marking representation respective of the position input, according to a real-time organ timing signal of an inspected organ of the body;

maneuvering the catheter through the lumen, toward the selected position, according to the current position relative to the position input; and producing an output when the current position substantially matches the selected position.

BRIEF DESCRIPTION OF THE DRAWINGS

The disclosed technique will be understood and appreciated more fully from the following detailed description taken in conjunction with the drawings in which:

FIG. 2A is a schematic illustration of the GUI of FIG. 1A, displaying a set of marks respective of a selected position within the lumen system and a representation of the current position of a stent advancing toward the selected location, on the two-dimensional image of FIG. 1A;

FIG. 2B is a schematic illustration of the GUI of FIG. 1B, displaying another set of marks equivalent to the set of marks of FIG. 2A, and another representation of the current position of the stent, on the three-dimensional image of FIG. 1B;

FIG. 4A is a schematic illustration of a two-dimensional image of the lumen of FIG. 1A, at activity-state $T_1$ of an inspected organ;

FIG. 4B is a schematic illustration of another two-dimensional image of the lumen of FIG. 1A at activity-state $T_2$;

FIG. 4C is a schematic illustration of a further two-dimensional image of the lumen of FIG. 1A at activity-state $T_3$;

FIG. 4D is a schematic illustration of a GUI which includes a real-time substantially stabilized representation of an MPS sensor of a catheter located within the lumen of FIG. 1A, superimposed on the lumen of FIG. 4B, the GUI being constructed and operative according to a further embodiment of the disclosed technique;

FIG. 10B is a schematic illustration of some of the three-dimensional volumes of FIG. 10A, at a later stage of image reconstruction;

FIG. 12 is a schematic illustration of an ECG coordinated display (i.e., a GUI) of a lumen, constructed and operative in accordance with a further embodiment of the disclosed technique;

FIG. 15B is a schematic illustration of a respiratory trajectory in a mechanical signal representation;

DETAILED DESCRIPTION OF THE EMBODIMENTS

The disclosed technique overcomes the disadvantages of the prior art by graphically designating on an image of the lumen, the position where the stent has to be delivered, and indicating when the stent has reached the selected position. A medical positioning system (MPS) sensor constantly detects the position of the stent relative to the selected position, and this position is represented on a pseudo-real-time image or a frozen (i.e., frozen in time) image of the lumen, without having to radiate the inspected organ of the patient repeatedly. The medical staff can either guide the catheter manually according to feedback from an appropriate user interface, such as display, audio output, and the like, or activate a catheter guiding system which automatically guides the catheter toward the selected position.

The term "position" herein below, refers to the location of a point in space, the orientation of the point in space, or a combination thereof. The term "lumen" herein below, refers to an organic tubular structure of the human patient or the operated animal, such as an artery, vein, cardiac vessel, brain vessel, part of the urogenital system, nephrotic system, hepatic system, bronchus tree, and the like. The term "medical operational element" herein below refers to an element which is employed to perform a minimally invasive operation within a lumen of the body of a patient. The medical operational element can be an expansion unit such as a balloon, stent, balloon expanding stent, an ablation unit such as laser, cryogenic fluid unit, electric impulse unit, cutting balloon, rotational atherectomy unit (i.e., rotablator), directional atherectomy unit, transluminal extraction unit, a substance delivery unit such as coated stent, drug delivery balloon, brachytherapy unit, and the like.

The term "organ timing signal" herein below, refers to a signal representing cardiac cycle of the heart or the respiratory cycle of the lungs. An organ timing signal can be extracted using traditional methods such as ECG or by measuring the movements of the lumen due to cardiac or respiratory cycles. The term "cine-loop" herein below, refers to a prerecorded sequence of two-dimensional images of the lumen, which are played back over and over again (i.e., in a loop), in synchrony with the real-time organ timing signal of the inspected organ of the patient. The two-dimensional images are acquired by a two-dimensional image acquisition device, such as X-ray fluoroscopy, C-arm, and the like, and individually stored while being associated with the respective activity-state of the inspected organ, at the time of image acquisition.

Figure 1B:
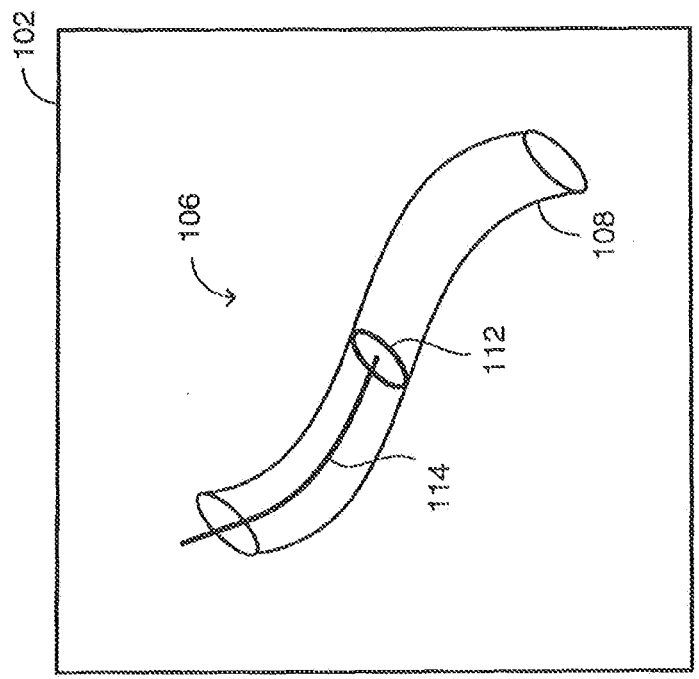
FIG. 1B is a schematic illustration of a GUI displaying another representation of the catheter on a three-dimensional image of a lumen of the lumen system of FIG. 1A, constructed and operative according to another embodiment of the disclosed technique.
Figure 1A:
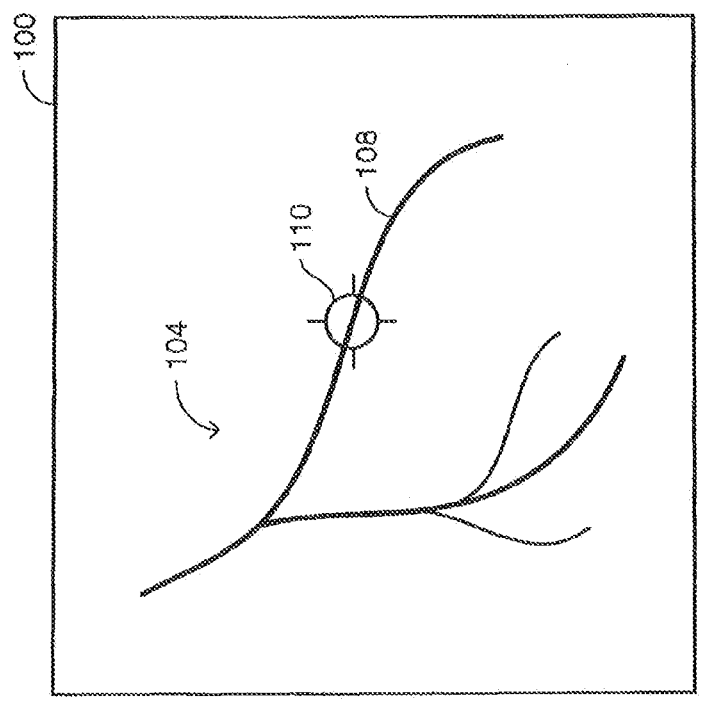
FIG. 1A is a schematic illustration of a graphical user interface (GUI) displaying a representation of a catheter on a two-dimensional image of a lumen system of the body of a patient, constructed and operative according to an embodiment of the disclosed technique.
Figure 3B:
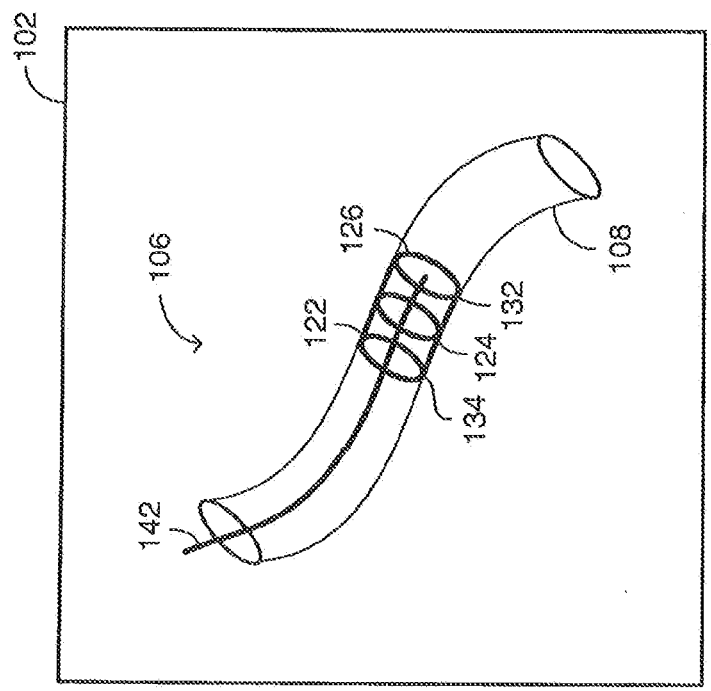
FIG. 3B is a schematic illustration of the GUI of FIG. 1B when the stent reaches the selected position.
Figure 3A:
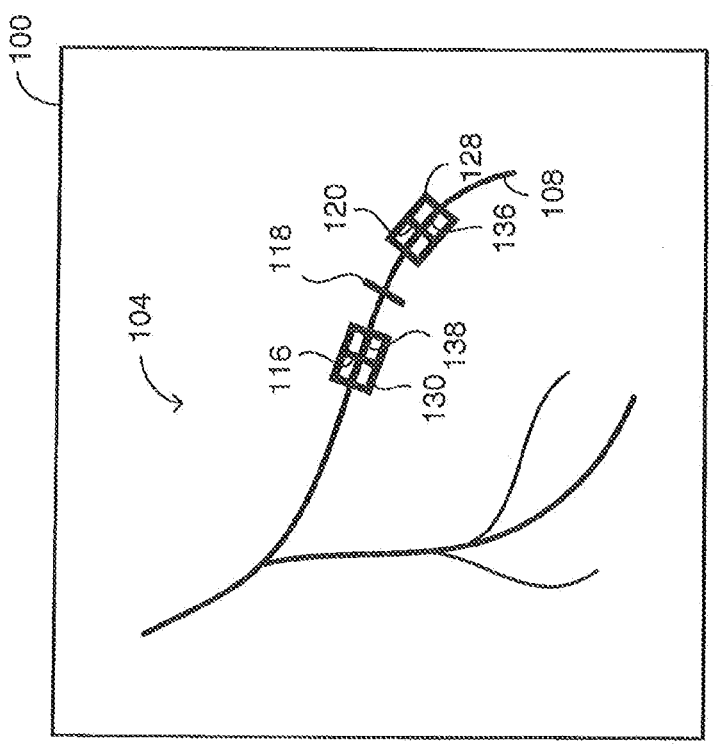
FIG. 3A is a schematic illustration of the GUI of FIG. 1A when the stent reaches the selected position.

Reference is now made to FIGS. 1A, 1B, 2A, 2B, 3A, and 3B. FIG. 1A is a schematic illustration of a graphical user interface (GUI) generally referenced 100, displaying a representation of a catheter on a two-dimensional image of a lumen system of the body of a patient, constructed and operative according to an embodiment of the disclosed technique. FIG. 1B is a schematic illustration of a GUI generally referenced 102, displaying another representation of the catheter on a three-dimensional image of a lumen of the lumen system of FIG. 1A, constructed and operative according to another embodiment of the disclosed technique. FIG. 2A is a schematic illustration of the GUI of FIG. 1A, displaying a set of marks respective of a selected position within the lumen system and a representation of the current position of a stent advancing toward the selected location, on the two-dimensional image of FIG. 1A. FIG. 2B is a schematic illustration of the GUI of FIG. 1B, displaying another set of marks equivalent to the set of marks of FIG. 2A, and another representation of the current position of the stent, on the three-dimensional image of FIG. 1B. FIG. 3A is a schematic illustration of the GUI of FIG. 1A when the stent reaches the selected position. FIG. 3B is a schematic illustration of the GUI of FIG. 1B when the stent reaches the selected position.

With reference to FIG. 1A, while a lumen system (e.g., the coronary arteries—not shown) of the body of a patient (not shown) is imaged by a plurality of two-dimensional image acquisition devices (not shown), the operator (i.e., physical staff) inserts a catheter (not shown) into the lumen system. The catheter can be of any type known in the art, such as guidewire, guiding catheter, balloon catheter, and the like. GUI 100 includes a two-dimensional image 104 (e.g., an X-ray fluoroscopy, angiogram) of the lumen system, as detected by the respective two-dimensional image acquisition device.

Two-dimensional image 104 is a real-time image which is acquired from the lumen system, while a contrast agent is present in the lumen system. Alternatively, two-dimensional image 104 is a cine-loop of the lumen system (i.e., a pseudo-real-time two-dimensional image). Further alternatively, two-dimensional image 104 is a frozen image of the lumen system (i.e., one of the images among a plurality of images in a cine-loop, which the operator selects). In this case, the selected two-dimensional image can be an image whose contrast for example, is better (e.g., exhibits better contrast) than all the rest, and which portrays the lumen system in a manner which is satisfactory for the operator either to designate the selected location of the stent, or to view a real-time representation of the stent, as the stent is being navigated within the lumen system.

With reference to FIG. 1B, GUI 102 includes a three-dimensional image 106 of a lumen (referenced 108) of the lumen system displayed in GUI 100, through which the catheter is being maneuvered. Three-dimensional image 106 is reconstructed from a plurality of two-dimensional images which are detected by respective the two-dimensional image acquisition device, during an image acquisition stage, as described herein below in connection with FIGS. 6, 7A, 7B, 8, 9, 10A, 10B, and 10C.

Three-dimensional image 106 is a pseudo-real-time image of lumen 108 (i.e., a three-dimensional cine-loop), which is played back in a loop, in synchrony with the real-time organ timing signal of the inspected organ. Alternatively, three-dimensional image 106 is a static image of lumen 108, which is selected among a plurality of three-dimensional images in the cine-loop. The operator can select the static image by playing the cine-loop forward and backward. Further alternatively, three-dimensional image 106 is an image of lumen 108, frozen at a selected activity-state of the inspected organ.

Three-dimensional image 106 is synchronized with a real-time organ timing signal (e.g., cardiac cycle) respective of the movement of the inspected organ (e.g., the inspected lumen—not shown). The organ timing signal can be acquired for example, by an ECG monitor (not shown) coupled with the patient. Alternatively, the organ timing signal (e.g., the heart beat or the respiration of the patient) can be determined by the MPS (not shown), as described herein below in connection with FIGS. 14, 15A, and 15B.

A system according to the disclosed technique can display a selected image sequence (either a sequence of two-dimensional images detected by the respective two-dimensional image acquisition device, or a sequence of three-dimensional images reconstructed from a plurality of two-dimensional images—i.e., a cine-loop or video clip), in synchrony with the real-time organ timing signal of the patient, among a list of prerecorded image sequences. The system can display a still image among a selected image sequence. Alternatively, the system can display a real-time two-dimensional image of an organ of the patient, acquired from a first viewing angle by one of the two-dimensional image acquisition devices, alongside a pseudo-real-time two-dimensional image sequence (i.e., two-dimensional cine-loop) of the inspected organ, acquired previously by either the same two-dimensional image acquisition device or another two-dimensional image acquisition device, from a second viewing angle, and played back in synchrony with the real-time organ timing signal of the inspected organ.

The operator can view a prerecorded two-dimensional image sequence (e.g., an X-ray fluoroscopy) synchronized with the real-time organ timing signal of the organ, thereby obviating the need to inject a contrast agent repeatedly and subjecting the patient to unnecessary radiation. Alternatively, the system can display the image relative to a selected activity-state of the organ (i.e., a frozen image), as described herein below in connection with FIG. 12.

An MPS sensor (not shown) is firmly attached to the tip of the catheter. Three-dimensional image 106 is registered with two-dimensional image 104, such that each point in two-dimensional image 104 corresponds to a respective point in three-dimensional image 106. In this manner, the coordinates of each point in three-dimensional image 106 can be projected onto two-dimensional image 104. Alternatively, each point in two-dimensional image 104 can be transferred to three-dimensional image 106 (e.g., by acquiring a series of two-dimensional images from different viewing angles). A real-time representation 110 (FIG. 1A) of the MPS sensor is superimposed on lumen 108, as described herein below in connection with FIG. 6. A real-time representation 112 (FIG. 1B) of the MPS sensor is superimposed on three-dimensional image 106.

In addition to real-time representation 110, the operator can view one or more fiducial markers (e.g., metallic band) attached to the catheter, on a real-time two-dimensional image of lumen 108. This feature enables the operator to continue using the real-time two-dimensional image, even when little or no contrast agent exists within lumen 108.

A trajectory 114 (FIG. 1B) of the catheter as advanced through lumen 108 is constructed and represented in GUI 102, as described herein below in connection with FIGS. 11B, and 11C. Trajectory 114 is constantly updated in synchrony with the movement of lumen 108, according to the position data acquired by the MPS sensor. Moreover, in this manner, three-dimensional image 106 is displayed relative to the coordinate system of lumen 108. The movement of lumen 108 can be caused for example, by the heart beat, the respiration, contraction of nearby muscles of the patient, and the like.

The operator can switch between GUI 100 and GUI 102, or display both GUI 100 and GUI 102 side by side, via a user interface, such as a switch, foot pedal, and the like, as described herein below in connection with FIG. 6. The operator can direct the system to display a real-time two-dimensional image of the lumen system, for example, by pressing a foot pedal, thereby activating the respective two-dimensional image acquisition device. Alternatively, the operator can direct the system to display a two-dimensional cine-loop of the lumen system, instead of the real-time two-dimensional image of the lumen system, via the user interface. In this case, the system displays the two-dimensional cine-loop which was last played back. If the system includes no cine-loops (i.e., prerecorded time-tagged image sequences), then the system displays a cine-loop of the most recent real-time two-dimensional image. Further alternatively, the operator can direct the system to display the real-time two-dimensional image and a selected cine-loop, on the same display, side by side.

With the aid of GUI 100 and GUI 102, the operator maneuvers the catheter manually, in order to reach a predetermined region within the lumen system. Alternatively, the operator can employ an automatic system (not shown) for automatically maneuvering the catheter to the predetermined region, as described herein below in connection with FIGS. 16, and 17.

With reference to FIG. 2A, during a planning session, the operator graphically designates a plurality of marks 116, 118, and 120 on two-dimensional image 104, as a selected position within lumen 108, which a medical operational element (not shown) is to be delivered to. The operator performs the marking either on a frozen two-dimensional image of lumen 108, or on a frozen three-dimensional image of lumen 108.

During the planning session, a respective one of displays 214 displays a superposition of a trajectory of a catheter previously maneuvered through lumen 108, on an image of lumen 108. The trajectory can be displayed either on two-dimensional image 104 or three-dimensional image 106 (e.g., trajectory 114).

This trajectory can be obtained for example, by employing a guided intravascular ultrasound catheter (GIVUS—not shown), in an imaging session prior to the planning session. The GIVUS is a catheter which includes an image detector (e.g., ultrasound transducer) at the tip thereof, and an MPS sensor in the vicinity of the image detector. The operator maneuvers the GIVUS within the lumen, as far as physically possible, and then pulls the GIVUS back through the lumen. During the pull-back, the image detector detects a plurality of two-dimensional images of the inside of the lumen.

The system associates each of the two-dimensional images with the respective position of the image detector determined by the MPS, and with the respective activity-state of the inspected organ. The system can determine a cine-loop of the trajectory during the pull-back, and the operator can select a frozen trajectory to be employed during the planning session. The system can further reconstruct three-dimensional image 106 according to the time-tagged two-dimensional images acquired by the GIVUS.

During the planning session, a respective one of displays 214 displays marks 116, 118 and 120 articulated by the user interface on an image of lumen 108. The operator can move marks 116, 118 and 120 together along the full length of the trajectory (e.g., trajectory 114 of FIG. 1B). Mark 118 designates the middle of the stent, while marks 116 and 120 designate the rear end and the front end of the stent, respectively.

The system determines the distance between marks 116 and 120, according to the type (i.e., size) of stent which the operator has selected to mount within lumen 108. Marks 116, 118 and 120 together, are locked-on to the trajectory, while being operative to travel along the trajectory. The operator designates the position of mark 118 along the trajectory where the stent is to be mounted within lumen 108.

For simplicity, the medical operational element in the example set forth in FIGS. 2A, 2B, 3A, and 3B, is a stent. In this case, each of marks 116, 118, and 120 is a substantially straight line, which is substantially perpendicular to lumen 108. For example, marks 116 and 120 designate the two ends of the stent, while mark 118 designates the middle of the stent. Marks 116, 118, and 120 define the location of the stent in lumen 108, as well as the orientation thereof. The marking is performed via a user interface (not shown), such as a joystick, push button, pointing device (e.g., a mouse, stylus and digital tablet, track-ball, touch pad), and the like.

A plurality of marks 122, 124 and 126, which are the counterpart of marks 116, 118, and 120, respectively, are simultaneously displayed on three-dimensional image 106 in GUI 102. For the purpose of performing the marking, each of two-dimensional image 104 and three-dimensional image 106 is frozen at the same activity-state of the inspected organ (e.g., the heart). This freezing feature provides a still image of lumen 108, thereby preventing vibrations of the image and enabling a successful marking by the operator.

Instead of manually designating the marks, an algorithm can be employed to automatically identify the selected location (e.g., by entering into the algorithm, a selected percentage of occlusion by a plaque in a lumen), and designate marks 116, 118, 120, 122, 124, and 126, automatically. This aspect of the invention is described herein below in connection with FIGS. 13A, 13B, and 13C. The system associates the occlusion data with three-dimensional image 106, and projects this occlusion data on two-dimensional image 104, for the purpose of designating marks 116, 118 and 120.

During the operation, following the planning session, a catheter which includes a stent (not shown), is maneuvered within lumen 108 toward marks 116, 118 and 120. An MPS sensor (not shown) is attached to the catheter in the vicinity of the stent. With reference to FIGS. 2A and 2B, the position of the front end and of the rear end of the stent are represented in real-time, by features 128 and 130, respectively, on two-dimensional image 104, and by features 132 and 134, respectively, on three-dimensional image 106. In the example set forth in FIGS. 2A and 2B, each of features 128 and 130 is in form of a rectangle with longitudinal lines 136 and 138, respectively, dividing each rectangle in two. The actual trajectory of the catheter is represented by a feature 140 (FIG. 2B) superimposed on three-dimensional image 106. The actual trajectory of the catheter can be represented by another feature (not shown) superimposed on two-dimensional image 104.

During the medical operation, the system superimposes features 128 and 130 together with marks 116, 118 and 120, while the catheter is being maneuvered through lumen 108, either on a real-time two-dimensional image of lumen 108 (e.g., angiogram), on a two-dimensional cine-loop of lumen 108, or on a frozen two-dimensional image of lumen 108. Additionally, the system superimposes features 132 and 134 together with marks 122, 124 and 126, while the catheter is being maneuvered through lumen 108, either on a pseudo-real-time three-dimensional image of lumen 108, or on a frozen three-dimensional image of lumen 108.

The system determines the distance between the centers (not shown) of features 128 and 130, according to the type (i.e., size) of stent which the operator selects for mounting in lumen 108. This distance as displayed on the respective one of displays 214, is substantially fixed, as the stent is maneuvered through lumen 108. Features 128 and 130 move together on image 104, while the stent is maneuvered through lumen 108. A respective one of displays 214 can display trajectories 140 and 142, either while catheter 222 is being maneuvered through lumen 108, or during a play-back session, after performing the medical operation on the patient.

It is noted that the system superimposes features 128, 130, 132, and 134, and marks 116, 118, 120, 122, 124, and 126, on the respective image of lumen 108, according to the real-time organ timing signal of the inspected organ (i.e., the system takes into account the movements of lumen 108 due to the movements of the inspected organ, while catheter 222 is being maneuvered through lumen 108). This aspect of the disclosed technique enables the system to display marks (116, 118, 120, 122, 124, and 126, on a vibrating image of lumen 108, at substantially the same position which the operator had initially designated relative to lumen 108. If the system did not operate in this manner, then marks 116, 118, 120, 122, 124, and 126, would be non-stationary relative to a vibrating image of lumen 108. Likewise, features 128, 130, 132, and 134, are substantially stationary relative to the vibrating image of lumen 108.

It is further noted that the operator can direct the system to either turn on or turn off the display of superposition of any of the marks, the representation of the position of the stent, the trajectory, or a combination thereof, via the user interface. Any attribute can be selected to represent the marks and the representation of the stent, as long as they are different, such as color, shape, size, and the like. However, a mark or a stent representation is displayed by the same attribute both in two-dimensional image 104 and three-dimensional image 106. For example, marks 116, 118, 120, 122, 124, and 126 are represented in green, features 128, 130, 132, and 134 are represented in blue, and trajectory 140 is represented in red.

With reference to FIGS. 3A and 3B, while the catheter is being maneuvered through lumen 108, each of two-dimensional image 104 and three-dimensional image 106, is displayed relative to the coordinate system of lumen 108 (i.e., relative to the MPS sensor which is attached to the catheter, and which constantly moves together with lumen 108). When the stent reaches the selected position (i.e., front end of the stent is substantially aligned with mark 120 and the rear end thereof is substantially aligned with mark 116), a user interface (e.g., audio, visual, or tactile device—not shown) announces the event to the operator.

In the example set forth in FIG. 3A, when the stent is aligned with the selected position, each pair of longitudinal lines and marks turns into a cross (i.e., longitudinal line 136 together with mark 120 forms one cross, and longitudinal line 138 together with mark 116 forms another cross). Additionally, the user interface can produce a relatively weak output, or a relatively strong output, when the stent is receding from the selected location, or approaching the selected location, respectively. A trajectory of the catheter while being maneuvered toward the selected location, is represented by a feature referenced 142 (FIG. 3B) superimposed on three-dimensional image 106.

Reference is further made to FIGS. 4A, 4B, 4C, and 4D. FIG. 4A is a schematic illustration of a two-dimensional image, generally referenced 144, of the lumen of FIG. 1A, at activity-state $T_1$ of an inspected organ. FIG. 4B is a schematic illustration of another two-dimensional image, generally referenced 146, of the lumen of FIG. 1A at activity-state $T_2$. FIG. 4C is a schematic illustration of a further two-dimensional image, generally referenced 148, of the lumen of FIG. 1A at activity-state $T_3$. FIG. 4D is a schematic illustration of a GUI generally referenced 150, which includes a real-time substantially stabilized representation of an MPS sensor of a catheter located within the lumen of FIG. 1A, superimposed on the lumen of FIG. 4B, the GUI being constructed and operative according to a further embodiment of the disclosed technique.

Two-dimensional images 144, 146 and 148 belong to a set of two-dimensional images of lumen 108 (FIG. 1A), acquired prior to the planning session. With reference to FIG. 4B, lumen 108 at activity-state $T_2$, represented by a point 152 has moved by a distance $S_1$ along the negative Y axis, relative to the position thereof at activity-state $T_1$. With reference to FIG. 4C, lumen 108 at activity-state $T_3$ has moved by a distance $S_2$ along the negative Y axis, relative to the position thereof at activity-state $T_2$.

The contrast agent which is injected into the lumen system of the patient remains within lumen 108 for a substantially short period of time. During this period of time, the contrast of the set of two-dimensional images gradually increases to a peak and then gradually decrease, until the two-dimensional image disappears altogether. The operator selects one of two-dimensional images 144, 146 and 148 (e.g., two-dimensional image 146, whose contrast is best among all others), in order to designate marks 116, 118 and 120 (FIG. 2A), and later observe the real-time advancement of the catheter represented by features 128 and 130, superimposed on two-dimensional image 146.

Two-dimensional image 146 (FIG. 4D) is a frozen image of lumen 108 at activity-state $T_2$. The system compensates for the movement of lumen 108 due to the cycle of the inspected organ (e.g., the cardiac cycle), in order to superimpose a substantially static real-time representation of the stent on frozen image 146 of lumen 108, in GUI 150. The system takes into account the distances $S_1$ and $S_2$ at the respective activity-states, for compensating for the movements of the MPS sensor due to the cardiac cycle.

With reference to FIG. 4D, GUI 150 displays a real-time representation 154 of the stent superimposed on an image of lumen 108 frozen at activity-state $T_2$, while representation 154 is substantially static at all activity-states, including activity-states $T_1$ and $T_2$. It is noted that according to this aspect of the disclosed technique, the system is capable to display a substantially static representation of the stent, substantially free of vibrations due to the cardiac cycle. In this manner, the system maintains a superposition of representation 154 on the image of lumen 108, within the boundaries of that image, while the catheter is maneuvered through lumen 108. In case the movements due to the cardiac cycle were not compensated, the representation 154 would move back and forth between points 156 and 158 (corresponding to distances $S_1$ and $S_2$, respectively), which are distracting to the operator.

Alternatively, the system can superimpose only that representation of the stent, which corresponds to the activity-state respective of the frozen image of lumen 108, and neglect all other activity-states of lumen 108. With reference to FIG. 4D, the system can superimpose representation 154 on the image of lumen 108, only when representation 154 corresponds to activity-state $T_2$. This type of display still provides a substantially satisfactory view for the operator, since for example, at substantially rapid rates of the cardiac cycle, this loss of data is substantially imperceptible to the human eye.

The system can determine the distances $S_1$ and $S_2$, according to a set of three-dimensional images reconstructed from a series of time-tagged two-dimensional images of lumen 108, acquired from inside of lumen 108 (e.g., by employing a GIVUS). Alternatively, the system can determine the distances $S_1$ and $S_2$ by processing and comparing among a set of two-dimensional images acquired from outside of lumen 108 (e.g., images 144, 146 and 148).

The operator can direct the system to switch between GUI 150 and a real-time two-dimensional image of lumen 108 (e.g., an angiogram), by employing a user interface (not shown—for example a foot pedal). When the operator presses the foot pedal, the two-dimensional image acquisition device radiates a portion of the body of the patient, and the system displays the real-time two-dimensional image instead of GUI 150. Alternatively, the system can superimpose the real-time two-dimensional image on GUI 150. Further alternatively, the system can display the real-time two-dimensional image along side GUI 150.

Figure 5:
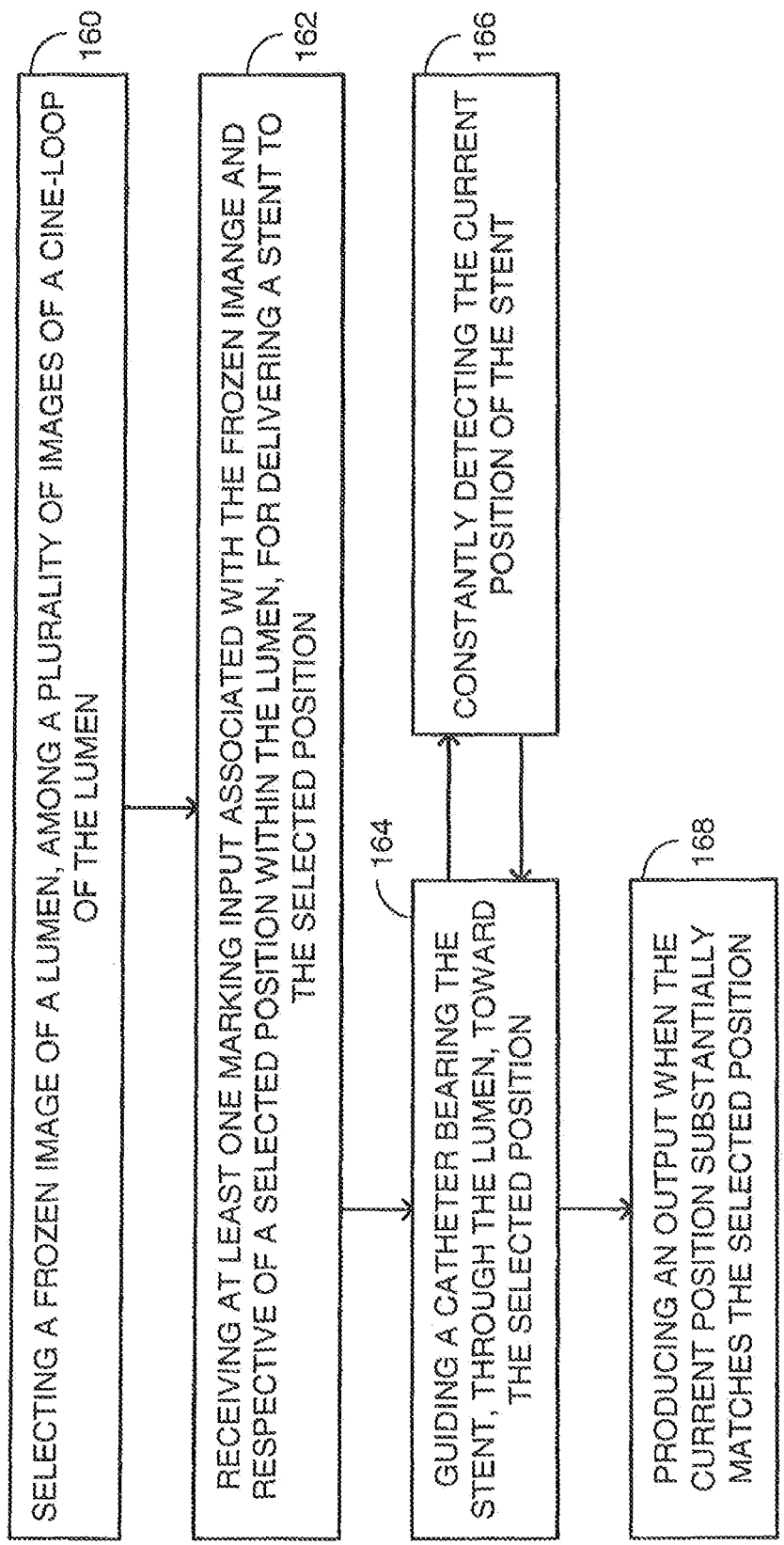
FIG. 5 is a schematic illustration of a method for delivering a stent to a selected position within a lumen, operative according to another embodiment of the disclosed technique.

Reference is now made to FIG. 5, which is a schematic illustration of a method for delivering a stent to a selected position within a lumen, operative according to another embodiment of the disclosed technique. In procedure 160, a frozen image of a lumen, among a plurality of images of a cine-loop of the lumen is selected. With reference to FIG. 2A, the operator selects two-dimensional image 104 among the images of a cine-loop of lumen 108, by viewing the cine-loop forward and backward.

In procedure 162, at least one marking input associated with the frozen image is received, respective of a selected position within the lumen, for delivering a stent to the selected position. With reference to FIG. 2A, a processor of a system receives via a user interface, data respective of marks 116, 118 and 120, which the operator designates on two-dimensional image 104. Marks 116, 118 and 120 designate the selected position within lumen 108, where the stent is to be delivered to. The processor determines the position of marks 122 (FIG. 2B), 124 and 126, equivalent to marks 116, 118 and 120, on three-dimensional image 106.

In procedure 164, a catheter bearing the stent, is guided through the lumen, toward the selected position. With reference to FIG. 2A, the operator guides the catheter with the stent attached to the tip thereof, through lumen 108 toward the selected position, while viewing representations 128 and 130 which represent the front end and the rear end of the stent, respectively, on GUI 100. The operator can view representations 132 (FIG. 2B) and 134, which are equivalent to representations 128 and 130, respectively, on GUI 102. Alternatively, the operator can activate an automatic guiding system, which automatically guides the catheter through lumen 108, according to the current position of the stent determined by the MPS, according to the selected position, and according to a topological representation of the lumen system.

In procedure 166, the current position of the stent is constantly detected. The MPS sensor which is attached to the catheter in the vicinity of the stent, constantly detects the current position of the stent. It is noted that procedures 164 and 166 are performed concurrently.

In procedure 168, an output is produced, when the current position substantially matches the selected position. With reference to FIG. 3A, when the stent reaches the selected position (i.e., rectangle 128 lines up with mark 120 and rectangle 130 lines up with mark 116), the user interface produces an announcement for the operator, according to an output of the processor.

Figure 6:
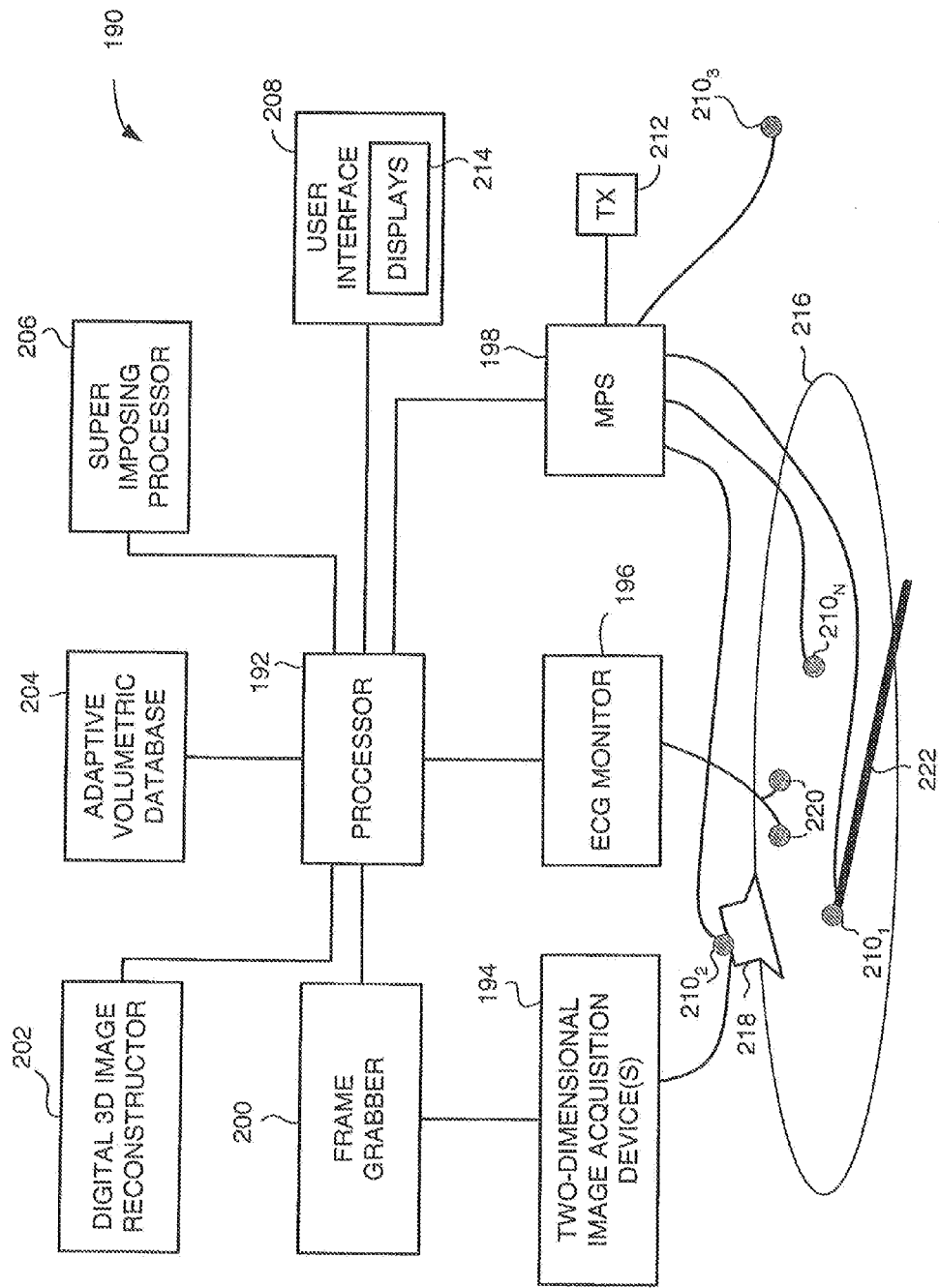
FIG. 6 is a schematic illustration of a multi functional three-dimensional imaging system constructed and operative in accordance with a further embodiment of the disclosed technique.

Reference is now made to FIG. 6, which is a schematic illustration of a multi functional three-dimensional imaging system, generally referenced 190, constructed and operative in accordance with a further embodiment of the disclosed technique. In the example set forth in FIG. 6, system 190 is adapted for producing a three-dimensional image sequence of lumen 108 (FIG. 1B), and playing it in real-time synchronicity, with the motion of the heart. However, system 190 can produce a three-dimensional image sequence of other organs (i.e., inspected organ) of the body of the patient, such as the brain, urogenital system, and the like. System 190 can be employed for marking on an image of lumen 108 (e.g., two-dimensional image 104 of FIG. 2A, or three-dimensional image 106 of FIG. 2B), a selected position within lumen 108 (e.g., marks 116, 118 and 120), for guiding a catheter toward the selected position, which carries a stent at a tip thereof.

System 190 can produce three-dimensional image 106 according to a plurality of two-dimensional images acquired by the two-dimensional image acquisition device, and according to the organ timing signal of lumen 108, and play back an image sequence of the three-dimensional image 106 in synchrony with the real-time organ timing signal. System 190 can play back also a cine-loop of lumen 108 in synchrony with the real-time organ timing signal, selected from a list of cine-loops. System 190 can display either of two-dimensional image 104 or three-dimensional image 106, relative to a selected activity-state of the organ timing signal (i.e., freezing an image).

System 190 can display either of two-dimensional image 104 or three-dimensional image 106, relative to the coordinate system of a selected MPS sensor (e.g., an MPS sensor attached to the catheter, an MPS sensor attached to the body of the patient, or an MPS attached to the operating table). System 190 can display a still image among a selected cine-loop. System 190 can acquire the organ timing signal by processing the MPS data, instead of the data acquired by the ECG monitor. System 190 can display a representation of the position of the catheter superimposed on either two-dimensional image 104, or three-dimensional image 106, as well as the actual trajectory of the catheter within the lumen. System 190 can identify a plaque within lumen 108, having a selected percentage of occlusion, and automatically designate the position of the plaque by marks 116, 118 and 120.

Following is a description of reconstructing a three-dimensional image sequence of an inspected organ, from a plurality of two-dimensional images of the inspected organ, and an organ timing signal of the inspected organ. Three-dimensional imaging system 190 includes a processor 192, a plurality of two-dimensional image acquisition devices 194, an ECG monitor 196, an MPS 198, a frame grabber 200, a digital three-dimensional image reconstructor (D3DR) 202, an adaptive volumetric database (AVDB) 204, a superimposing processor 206, a user interface 208, a plurality of MPS sensors $210_1$, $210_2$, $210_3$ and $210_N$, and an MPS transmitter 212. User interface 208 includes a plurality of displays 214, a joystick (not shown), a push button (not shown), and a pointing device (not shown), such as a mouse, stylus and digital tablet, keyboard, microphone, and the like.

Each of displays 214 can be a two-dimensional display, an auto-stereoscopic display to be viewed with a suitable pair of spectacles, a pair of goggles, and the like. For example, one of displays 214 displays GUI 100 (FIG. 1A), while another one of displays 214 displays GUI 102 which includes a three-dimensional image of lumen 108, a two-dimensional ultrasound image of lumen 108 acquired by a GIVUS, an ECG representation, an appropriate task bar, and the like.

Two-dimensional image acquisition device 194 can be of any type known in the art, such as computerized tomography (CT), nuclear magnetic resonance (MRI), positron-emission tomography (PET), single-photon-emission tomography, fluoroscopy (i.e., X-ray machine), C-arm, guided intra-vascular ultrasound (GIVUS), and the like. Each of two-dimensional image acquisition devices 194 acquires either a two-dimensional image of lumen 108 (FIG. 1A) from outside of the body of the patient (e.g., by employing a C-arm, CT, MRI), or a two-dimensional image of lumen 108 from within lumen 108 (e.g., by employing a GIVUS).

A respective one of two-dimensional image acquisition devices 194 includes an image transducer 218. ECG monitor 196 continuously detects an electrical timing signal of the heart (not shown) during inspection or surgery procedure, by employing a plurality of ECG electrodes 220.

Adaptive volumetric database 204 stores data required by system 190. Adaptive volumetric database 204 is typically a database unit, which allows for storage and access of data records. The data includes frames of captured two-dimensional images from two-dimensional image acquisition devices 194, as well as MPS sensor readings from MPS 198. Data is transferred to adaptive volumetric database 204, from which the data is recalled for processing. Intermediate and final data values obtained throughout computations of processor 192 may also be stored in adaptive volumetric database 204. Adaptive volumetric database 204 may further store information from additional devices used in conjunction with system 190 (e.g., information from an external monitoring device such as ECG monitor 196, intra-vascular ultrasound—IVUS information, and the like). In general, adaptive volumetric database 204 stores all possible information that may be needed by system 190. Data elements that are stored in adaptive volumetric database 204 are time-tagged.

Processor 192 is coupled with ECG monitor 196, MPS 198, frame grabber 200, D3DR 202, superimposing processor 206, AVDB 204 and with user interface 208. Each of two-dimensional image acquisition devices 194 is coupled with frame grabber 200 and with image transducer 218. MPS 198 includes MPS transmitter 212 and MPS sensors $210_1$, $210_2$, $210_3$ and $210_N$. MPS sensor $210_1$ is firmly attached to the tip of a catheter 222. MPS sensor $210_2$ is firmly attached to image transducer 218. ECG electrodes 220 are attached to different locations on the body of patient 216. MPS sensor $210_N$ is firmly attached to the body of patient 216. MPS sensor $210_3$ is a reference sensor which is firmly attached to the operation table (not shown) on which patient 216 is lying. Each of MPS sensors $210_1$, $210_2$, $210_3$ and $210_N$ can be coupled with MPS 198 either by a conductor, or via a wireless link.

Image transducer 218 detects a plurality of two-dimensional images, each representing a slice of the inspected organ (i.e., the heart). Each of these two-dimensional images has a different spatial location and orientation.

Frame grabber 200 grabs each detected two-dimensional image and provides it to processor 192. MPS 198 receives and processes data related to the location and orientation of catheter 222 via MPS sensor $210_1$ and processes data related to the location and orientation of image transducer 218 via MPS sensor $210_2$. MPS 198 further receives and processes data related to the location and orientation of the body of patient 216, via MPS sensor $210_N$. It is noted that MPS sensor $210_N$ is used as reference in case patient 216 moves. MPS sensor $210_N$ is generally attached to an inspected area of a patient body (reference 216). It is noted that MPS 198 can include additional MPS sensors, to be used as further references, thereby enhancing the performance of system 190. It is noted however that other methods for assigning a reference point can be used, such as initial referencing between all of the MPS sensors, strapping patient 216 during the entire procedure, analyzing the acquired images, and identifying a recurring visual point or section therein for each of the MPS sensors other than the one for image transducer 218, and the like.

MPS 198 produces predetermined electromagnetic fields using MPS transmitter 212. Each of the MPS sensors $210_1$, $210_2$, $210_3$ and $210_N$ includes electromagnetic field detection elements, such as coils, for detecting the electromagnetic fields produced by MPS 198.

MPS 198 processes the detected electromagnetic fields and provides an indication of the three-dimensional location and orientation of MPS sensors $210_1$, $210_2$, $210_3$ and $210_N$. Hence, MPS 198 is operative to determine the location and orientation of image transducer 218, catheter 222 and a selected point on the body of patient 216.

The location and orientation of each of the captured two-dimensional images are directly derived from the location and orientation of image transducer 218. Hence, by determining the location and orientation of MPS sensor $210_2$, MPS 198 can determine the location and orientation of each of the two-dimensional images captured by image transducer 218.

ECG monitor 196 obtains and represents an electrical timing signal (ECG—electrocardiogram) of the inspected heart. It is noted that ECG is a heart timing signal, which includes ECG cycles and represents the propagation of electrical currents through specific regions of the heart. The duration of an ECG cycle (or cardiac cycle) is defined as the time between two subsequent heart contractions. ECG is detected using at least two ECG electrodes, which are placed on selected areas of the body of patient 216 (e.g., the arms, legs, chest, abdomen, and the like).

ECG electrodes 220 continuously obtain an electrical signal from the heart and provide this signal to ECG monitor 196. ECG monitor 196 amplifies the received electrical signal, produces a graphic line tracing the electrical activity of the heart, as a function of the time, and provides this data in digital format to processor 192.

Processor 192 receives each of the two-dimensional images, the respective three-dimensional location and orientation of that specific two-dimensional image, and the organ timing signal of the heart at the time the image was captured. Processor 192 can further receive the three-dimensional location and orientation of catheter 222. Processor 192 associates each detected two-dimensional image, with the location and orientation information and the heart-timing signal.

When catheter 222 is located within the inspected organ, a two-dimensional image can include a sliced representation of a portion thereof. Processor 192 receives the location and orientation of MPS sensor $210_1$, which is attached to catheter 222 and can extrapolate the location and orientation of a larger portion of catheter 222, in case that portion of catheter 222 is substantially rigid. Hence, processor 192 can determine if that portion of catheter 222 is located within an area of the acquired two-dimensional image. Processor 192 can discard this area, while updating the three-dimensional image, to which the two-dimensional image belongs.

D3DR 202 reconstructs a three-dimensional image from captured two-dimensional images, having the same activity-state (e.g., for each determined point of the heart timing cycle) and from the three-dimensional location and orientation data associated with each of the images.

AVDB 204 contains the reconstructed three-dimensional images of the inspected organ, along with the activity-state associated therewith and with the location and orientation of the coordinate system thereof. The detected ECG sequence is further used for synchronously playing back the three-dimensional images, where every three-dimensional image is displayed when the activity-state associated therewith is substantially equal to the real-time detected activity-state of the inspected organ.

In case catheter 222 is inserted in the heart, superimposing processor 206 can add the three-dimensional location and orientation of catheter 222 to the reconstructed three-dimensional image. Alternatively, processor 192 can extrapolate the shape of catheter 222 in the coordinate system of the reconstructed three-dimensional image.

A respective one of displays 214 presents a three-dimensional motion picture of lumen 108 in synchrony therewith, which can be considered a pseudo real-time simulation thereof. Processor 192 can determine the reference coordinate system of the display of the image (either real-time two-dimensional, or real-time three-dimensional), to be any of the following:

The coordinate system of patient 216, where the body of patient 216 is still and lumen 108 and catheter 222 move.

The coordinate system of lumen 108, where lumen 108 is still, and catheter 222 and the rest of body of patient 216 move. It is noted that this viewing coordinate system can be extremely useful in cases where lumen 108 exhibits rapid movement.

The coordinate system of catheter 222, where catheter 222 is still, and lumen 108 as well as the rest of the body of patient 216 move.

Figure 7A:
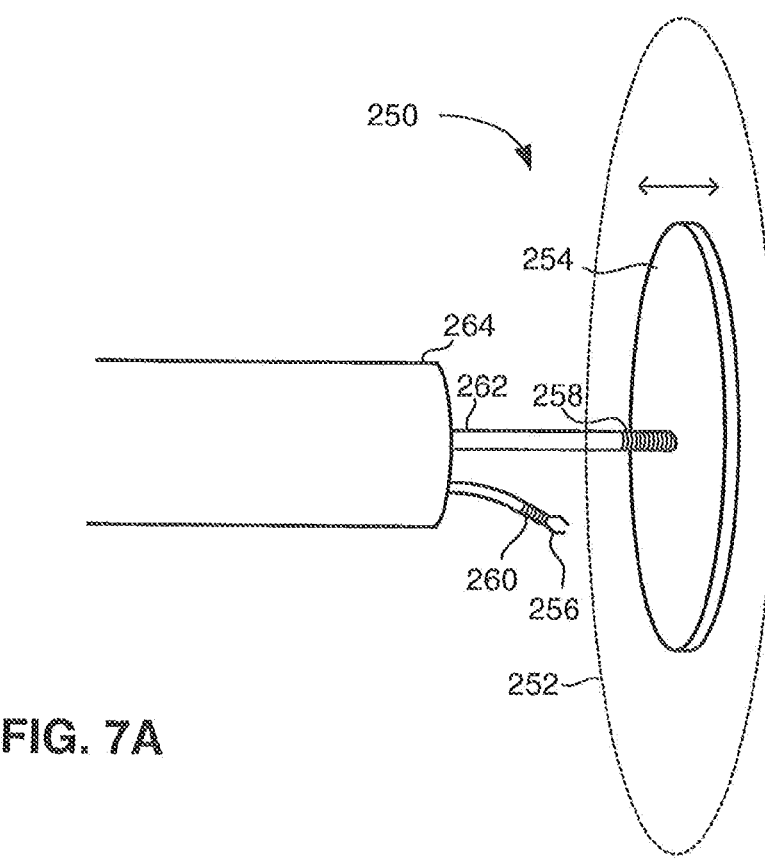
FIG. 7A is an illustration in perspective of an inner-body radial ultrasound imaging system, constructed and operative in accordance with another embodiment of the disclosed technique.
Figure 7B:
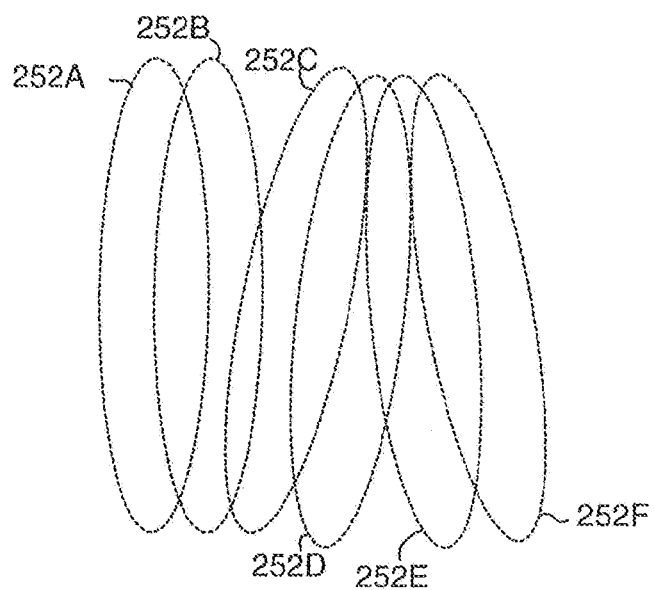
FIG. 7B is an illustration in perspective of a plurality of radial two-dimensional images of the inner walls of an inspected vessel.

Reference is further made to FIGS. 7A and 7B. FIG. 7A is an illustration in perspective of an inner-body radial ultrasound imaging system, generally referenced 250, constructed and operative in accordance with another embodiment of the disclosed technique. FIG. 7B is an illustration in perspective of a plurality of radial two-dimensional images of the inner walls of an inspected vessel, generally referenced 252.

System 250 includes an inner-body radial image transducer 254, a surgical tool (i.e., typically a minimally invasive surgical device) 256, MPS sensors 260 and 258, a mounting catheter 262 and a dilation catheter 264. It is noted that inner-body radial ultrasound imaging system 250 can be replaced with alternative ultrasound systems such as GIVUS, or other types of two-dimensional imaging systems.

Radial image transducer 254 is mounted on mounting catheter 262, which is further inserted in dilation catheter 264. MPS sensor 260 is located at a tip of mounting catheter 262 adjacent to radial image transducer 254. Mounting catheter 262 is inserted in dilation catheter 264. MPS sensor 260 is located in close proximity to the tip of surgical tool 256. Surgical tool 256 is further inserted in dilation catheter 264.

Radial image transducer 254 detects a plurality of two-dimensional images of different areas of the inspected organ (such as two-dimensional images 252A, 252B, 252C, 252D, 252E and 252F (FIG. 7B). MPS 198 (FIG. 6) detects the location and orientation of radial image transducer 254, using sensor 260. MPS 198 (FIG. 6) further detects the location and orientation of surgical tool 256, using sensor 260. The location and orientation of two-dimensional images 252A, 252B, 252C, 252D, 252E and 252F (FIG. 7B) are directly derived from the location and orientation of the transducer 254.

As can be seen in FIG. 7B, each of the detected two-dimensional images 252A, 252B, 252C, 252D, 252E and 252F is a two-dimensional representation of a different peripheral portion of the inspected area within the inspected organ and its vicinity. Radial image transducer 254 provides the detected two-dimensional images 252A, 252B, 252C, 252D, 252E and 252F to a respective one of two-dimensional image acquisition devices 194 (FIG. 6). System 190 (FIG. 6) associates each two-dimensional image, with the location and orientation thereof.

Figure 8:
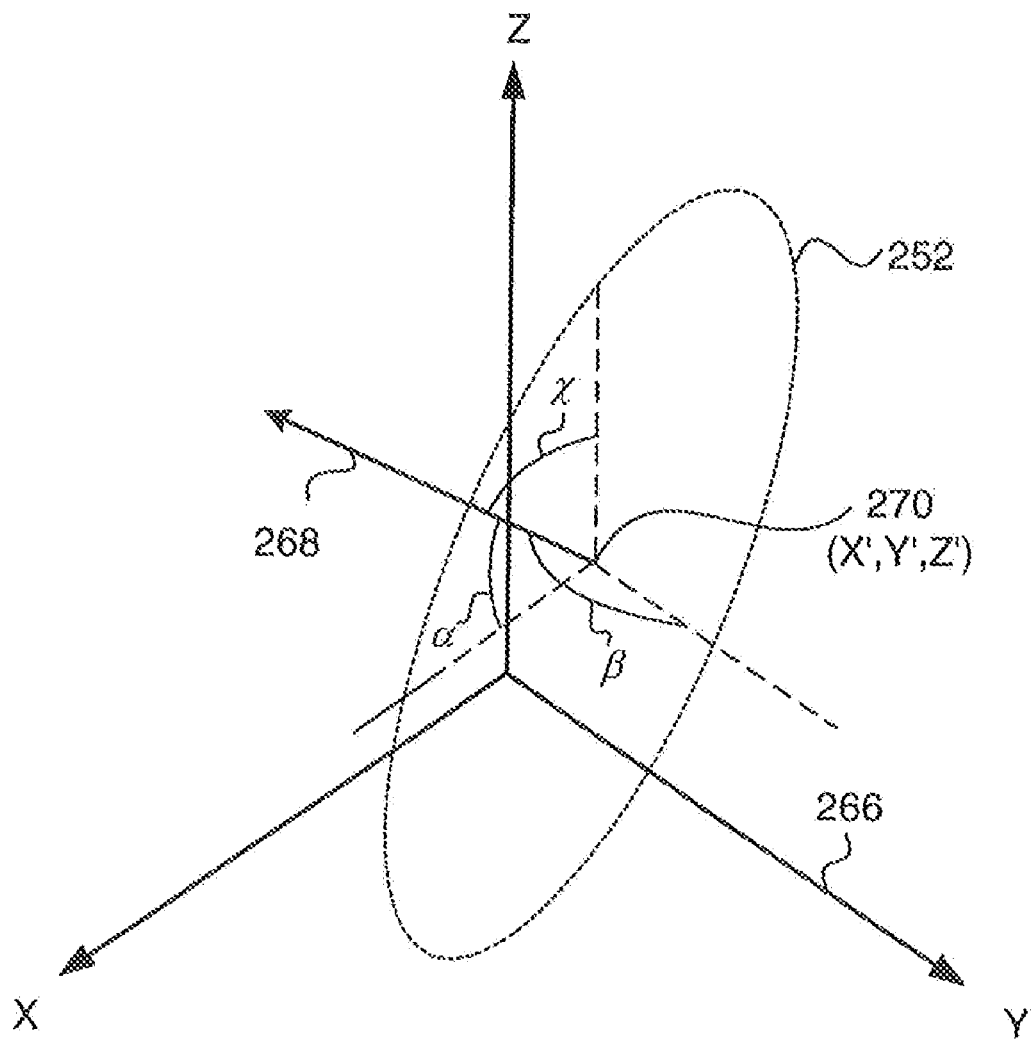
FIG. 8, which is a schematic illustration of a two-dimensional image in a given coordinate system.

Reference is further made to FIG. 8, which is a schematic illustration of a two-dimensional image, generally referenced 252, in a given coordinate system, generally referenced 266. FIG. 8 is mainly used for visualizing the terms "location" and "orientation" of the two-dimensional image 252 in coordinate system 266.

The location and orientation of each two-dimensional image 252 are determined in the coordinate system 266 (X, Y and Z). System 252 determines a selected point in each captured two-dimensional image, which is to be the reference point for that image. In the example set forth in FIG. 8, the center of the image is determined to be the reference location point thereof. A unit vector extending from that point, perpendicular to the plane of that image determines the orientation of that image.

Each detected two-dimensional image 252 is taken in a specific location (X', Y' and Z') and a specific orientation (angles $\alpha$, $\beta$, and $\chi$). A vector 268 extends from a selected point 270 of the image 252. The coordinates of this point X', Y' and Z' determine the specific three-dimensional location of the image 252 in the coordinate system 266. Angles $\alpha$, $\beta$, and $\chi$ are the angles between the vector 268 and each of the axes X, Y and Z, respectively. Thereby, vector 268 determines the specific three-dimensional orientation of image 252 in coordinate system 266.

Figure 9:
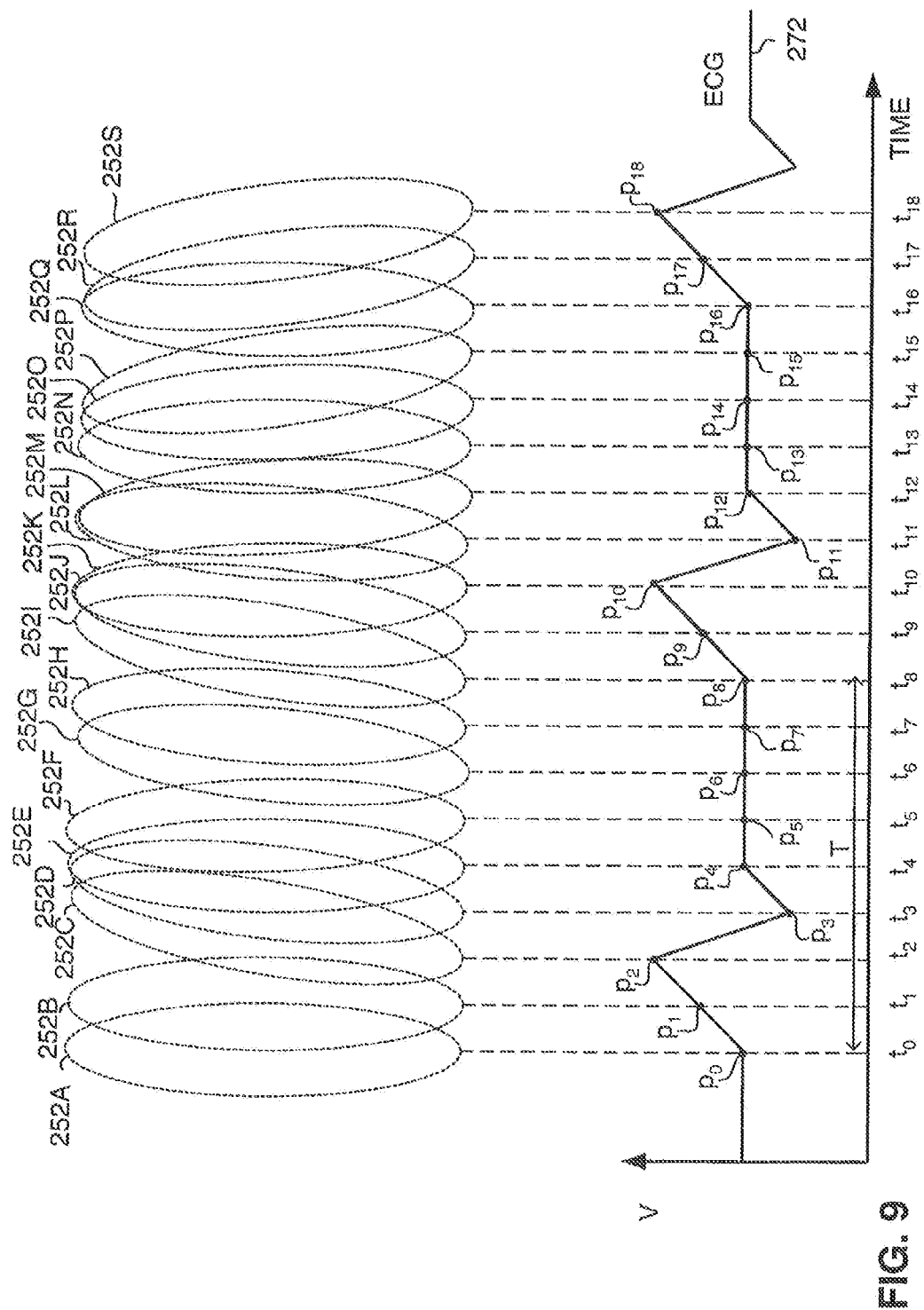
FIG. 9 is an illustration in perspective of a plurality of two-dimensional images and an organ timing signal.

Reference is further made to FIG. 9, which is an illustration in perspective of a plurality of two-dimensional images, generally referenced 252, and an organ timing signal, generally referenced 272. In the example set forth in FIG. 9, the organ timing signal is an ECG signal.

The ECG signal can be used for synchronizing the detection procedure of two-dimensional images 252A, 252B, 252C, 252D, 252E, 252F, 252G, 252H, 252I, 252J, 252K, 252L, 252M, 252N, 252O, 252P, 252Q, 252R and 252S, where each image is taken at a predetermined position in the organ timing signal. Two-dimensional images 252A, 252B, 252C, 252D, 252E, 252F, 252G, 252H, 252I, 252J, 252K, 252L, 252M, 252N, 252O, 252P, 252Q, 252R and 252S are detected at predefined points in time $t_0$, $t_1$, $t_2$, $t_3$, $t_4$, $t_5$, $t_6$, $t_7$, $t_8$, $t_9$, $t_{10}$, $t_{11}$, $t_{12}$, $t_{13}$, $t_{14}$, $t_{15}$, $t_{16}$, $t_{17}$ and $t_{18}$, respectively. T denotes the cycle duration of ECG signal 272 (e.g., the time interval between the time points $t_0$ and $t_8$). Each point $p_0$, $p_1$, $p_2$, $p_3$, $p_4$, $p_5$, $p_6$, $p_7$, $p_8$, $p_9$, $p_{10}$, $p_{11}$, $p_{12}$, $p_{13}$, $p_{14}$, $p_{15}$, $p_{16}$, $p_{17}$ and $p_{18}$ denotes a specific position on the ECG timing signal and is associated with specific activity-state of the heart.

In this example, two-dimensional images are detected continuously at a rate of eight images per ECG cycle into predetermined points in each heart cycle. Each point $p_0$, $p_1$, $p_2$, $p_3$, $p_4$, $p_5$, $p_6$, and $p_7$ denotes a specific position on the first ECG cycle, each point $p_8$, $p_5$, $p_{10}$, $p_{10}$, $p_{12}$, $p_{13}$, $p_{14}$ and $p_{15}$ denotes a specific position on the second ECG cycle, and the like. Points $p_a$ and $p_{16}$ have the same specific position on the ECG timing signal, as point $p_0$, and hence are associated with the same activity-state. Points $p_0$ and $p_{17}$ have the same specific position on the ECG timing signal, as point $p_1$, and hence are associated with the same activity-state. Points $p_{10}$ and $p_{18}$ have the same specific position on the ECG timing signal, as point $p_2$, and hence are associated with the same activity-state. Thus, each detected two-dimensional image is associated with a specific activity-state of the heart.

Figure 10A:
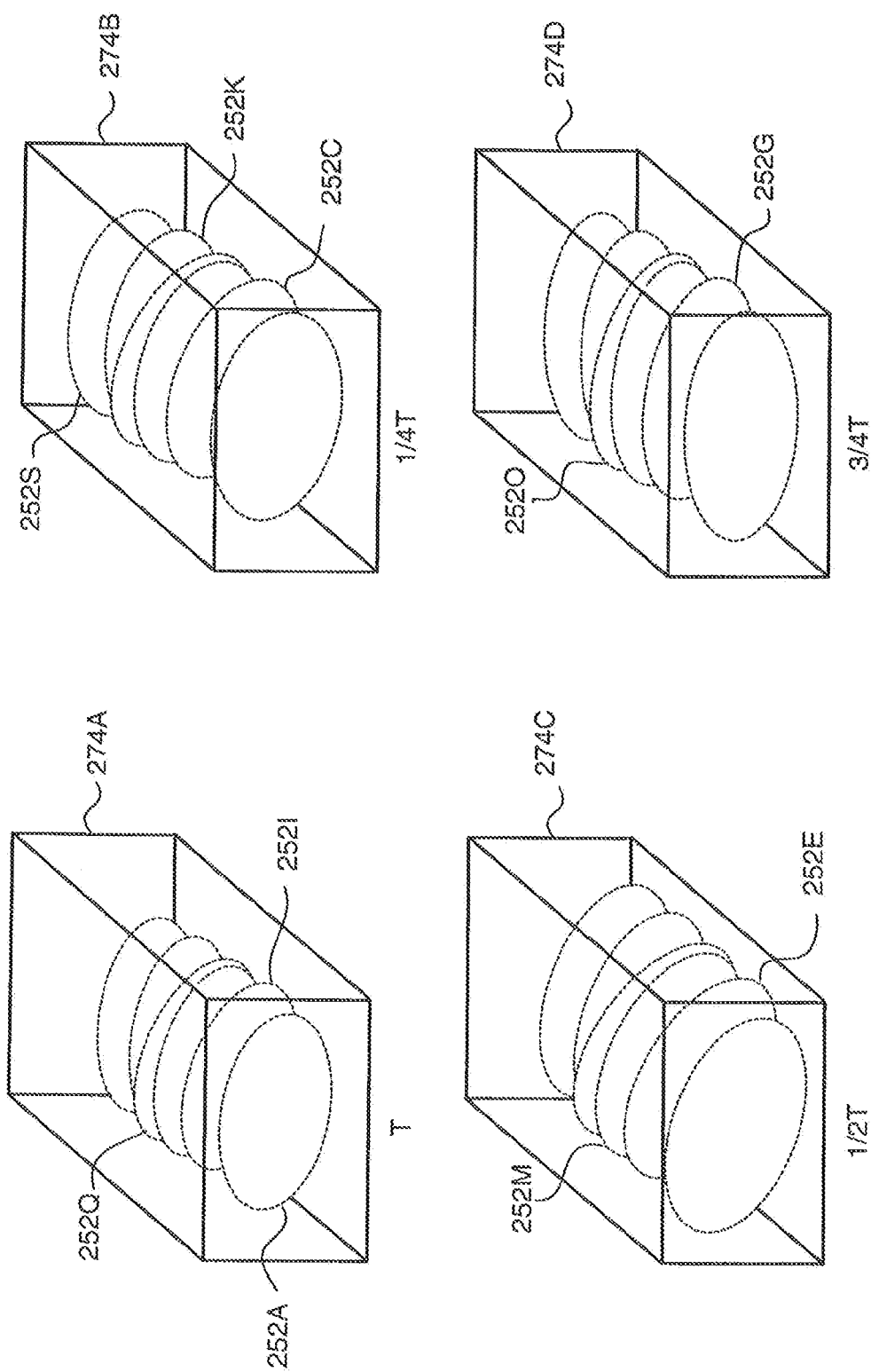
FIG. 10A is a schematic illustration of a plurality of three-dimensional volumes according to a further embodiment of the disclosed technique.
Figure 10C:
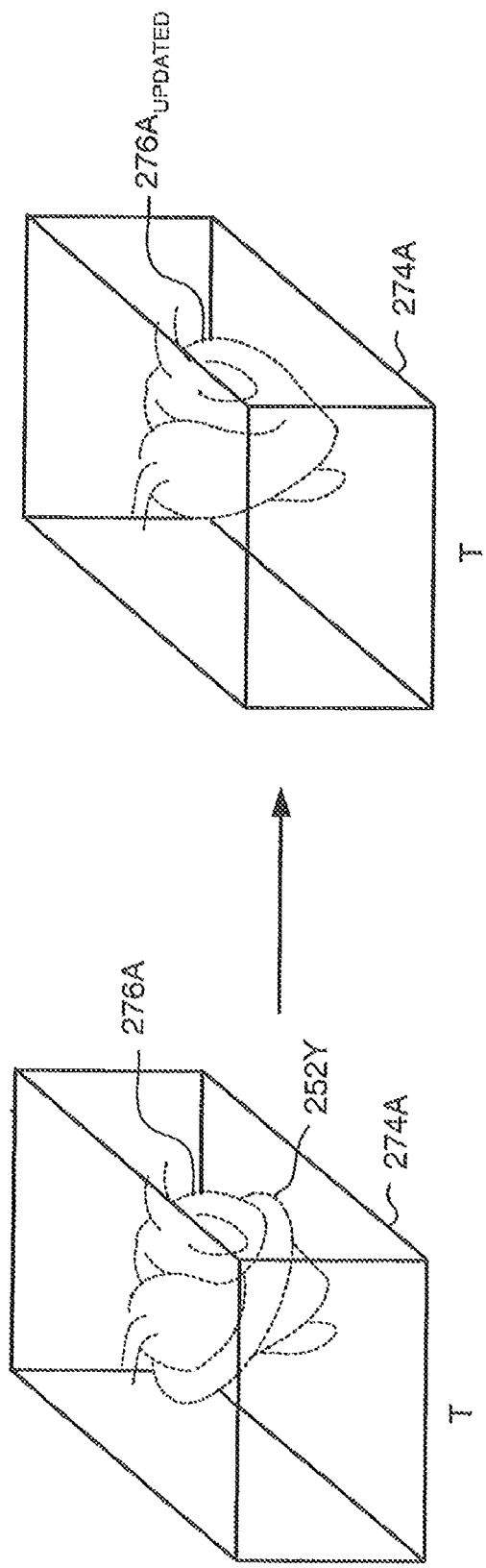
FIG. 10C is a schematic illustration of a selected three-dimensional volume of FIG. 10A, going through a procedure of image updating.

Reference is further made to FIGS. 10A, 10B, and 10C. FIG. 10A is a schematic illustration of a plurality of three-dimensional volumes, generally referenced 274, according to a further embodiment of the disclosed technique. FIG. 10B is a schematic illustration of some of the three-dimensional volumes of FIG. 10A, at a later stage of image reconstruction.

FIG. 10C is a schematic illustration of a selected three-dimensional volume of FIG. 10A, going through a procedure of image updating.

With reference to FIG. 10A, each of the three-dimensional volumes 274 is associated with a selected one of the specific positions in the organ timing signal cycle, and hence is associated with the respective activity-state. In the present example, three-dimensional volumes 274A, 274B, 274C and 274D are associated with organ timing signal cycle locations T, ¼T, ½T and ¾T, respectively.

Each of the three-dimensional volumes 274A, 274B, 274C and 274D is used for reconstructing a three-dimensional image for a selected location in the organ timing signal cycle, and hence for the respective activity-state. Processor 192 (FIG. 6) sorts the two-dimensional images according to the timing position of the image on ECG signal 272 (i.e., a specific activity-state).

In the present example, volume 274A includes two-dimensional images 252A, 252I and 252Q (FIG. 9), which were detected at time points $t_0$, $t_8$ and $t_{16}$, respectively. The position in the organ timing signal cycle of these images is T. Volume 274B includes two-dimensional images 252C, 252K and 252S (FIG. 9), which were detected at time points $t_2$, $t_{10}$ and $t_{18}$, respectively. The position in the organ timing signal cycle of these images is ¼ T. Volume 274C includes two-dimensional images 252E and 252M (FIG. 9), which were detected at time points $t_4$ and $t_{12}$, respectively. The position in the organ timing signal cycle of these images is ½T. Volume 274D includes two-dimensional images 252G and 252O (FIG. 9), which were detected at time points $t_6$ and $t_{14}$, respectively. The position in the organ timing signal cycle of these images is ¾ T.

At this point, volume 274A contains information relating to the two-dimensional images that were stored therein, while portions of volume 274A remain at zero value, since no two-dimensional image is related thereto. D3DR 202 (FIG. 6) analyzes the content of three-dimensional volume 274A and attempts to determine the value of some of these zero value portions, for example, by means of extrapolation. With reference to FIG. 10B, D3DR 202 (FIG. 6) reconstructs an image 276A within three-dimensional volume 274A. Similarly, D3DR 202 reconstructs image 276C within three-dimensional volume 274C.

System 190 (FIG. 6) updates the three-dimensional image 276A in real time. Processor 192 (FIG. 6) continuously receives two-dimensional images, associated with a location and orientation thereof and an organ activity-state. Processor 192 (FIG. 6) provides each of these two-dimensional images to D3DR 202 (FIG. 6) together with the three-dimensional volume, associated with the same organ activity-state. D3DR 202 updates the three-dimensional volume according to the values of the new two-dimensional images.

The update procedure can be performed in many ways. According to one aspect of the disclosed technique, a new value in a selected three-dimensional pixel (voxel) replaces an old value. According to another aspect of the disclosed technique, an updated voxel value includes a combination (linear or otherwise) of the old voxel value (i.e., which already exists in the three-dimensional volume) and the newly acquired value (i.e., received from the two-dimensional image). It is noted that system 190 can operate either using polygonal or voxel representations.

According to a further aspect of the disclosed technique, each of the voxels in the three-dimensional volume includes various attributes such as if the current value thereof, was provided from an acquired image, or was calculated in the process of reconstructing the three-dimensional image, by means of extrapolation. In this case, a newly acquired value is preferred over a calculated one. With reference to FIG. 10C, D3DR 202 receives a new two-dimensional image 252Y, which is associated with an organ activity state of t=T. D3DR 202 updates the respective three-dimensional volume 274A and the image therein 276A, thereby producing an updated image $276A_{UPDATED}$.

In case where a catheter 222 (FIG. 6) is inserted in the inspected organ, system 190 excludes a fragment of the two-dimensional image, which contains a representation of the catheter 222. Processor 192 (FIG. 6) modifies the two-dimensional image by excluding these fragments (e.g. by introducing null values to those fragments). D3DR 202 analyzes the modified two-dimensional image and does not update the respective portions in the respective three-dimensional volume.

It is noted that each ECG cycle consists of a period of relaxation, named a diastole followed by a period of contraction named a systole. The duration of the ECG cycle is defined as a time between two subsequent heart contractions. According to a further embodiment of the disclosed technique, the ECG cycle is evenly divided by N, where N denotes the number of three-dimensional images in the final image sequence.

Following is a description of reconstructing the trajectory of a catheter within a lumen, according to detected positions of the catheter at a selected activity-state of the organ timing signal of the lumen. In this manner, a trajectory corresponding to the selected activity-state, can be displayed together with the three-dimensional image of the lumen corresponding to the same activity-state. Alternatively, a real-time three-dimensional image sequence of the lumen can be displayed according to the organ timing signal of the lumen, together with the corresponding trajectories.

Figure 11A:
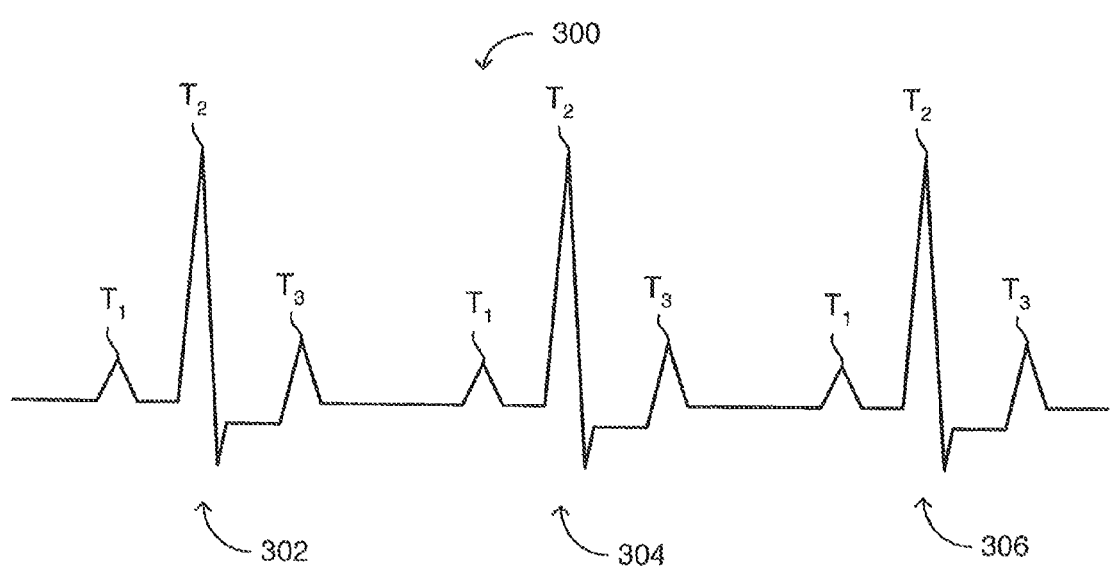
FIG. 11A is a schematic illustration of an ECG of a patient.
Figure 11B:
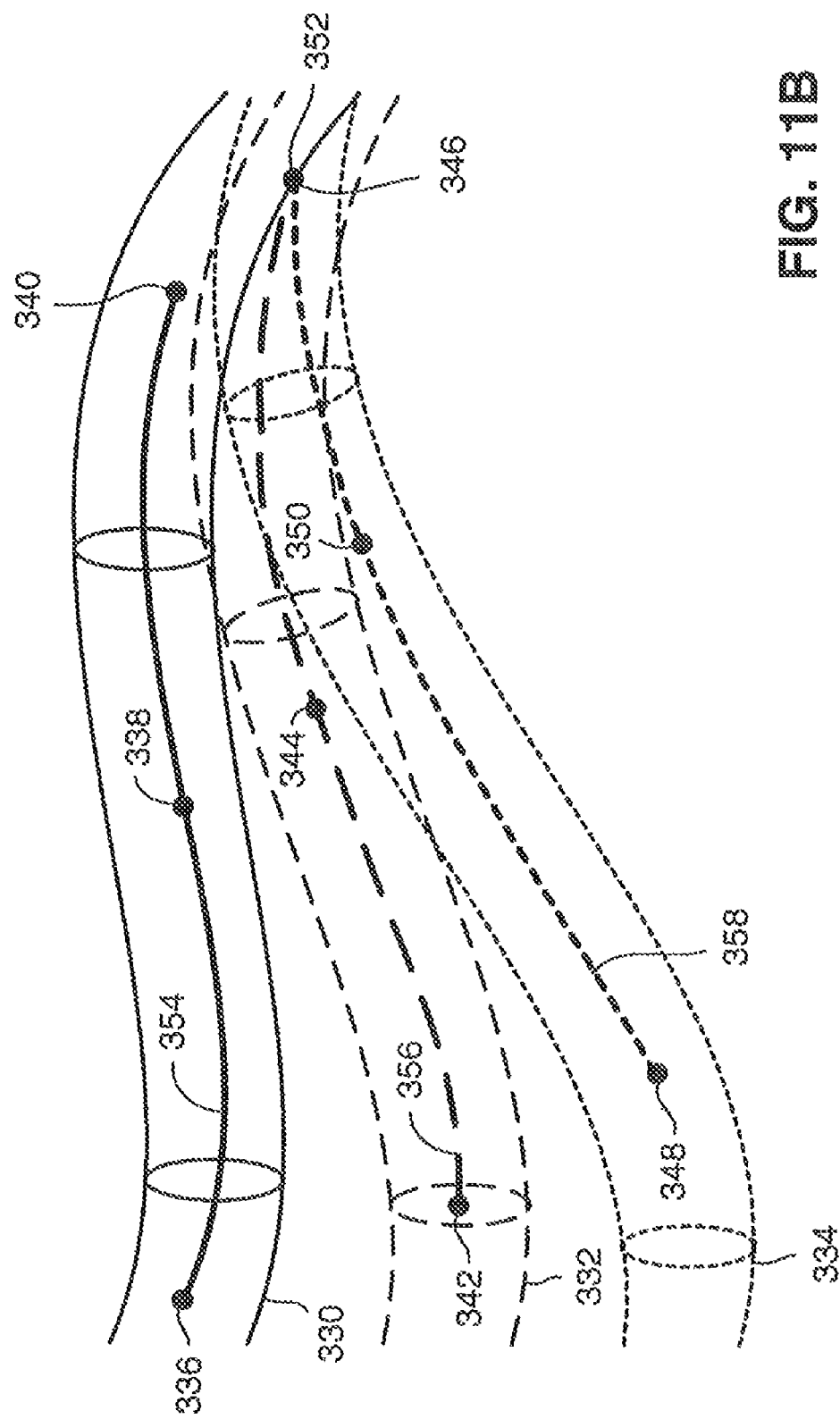
FIG. 11B is a schematic illustration of trajectories of the tip of the catheter of the system of FIG. 6, respective of different activity-states of the ECG of FIG. 11A, constructed according to another embodiment of the disclosed technique.
Figure 11C:
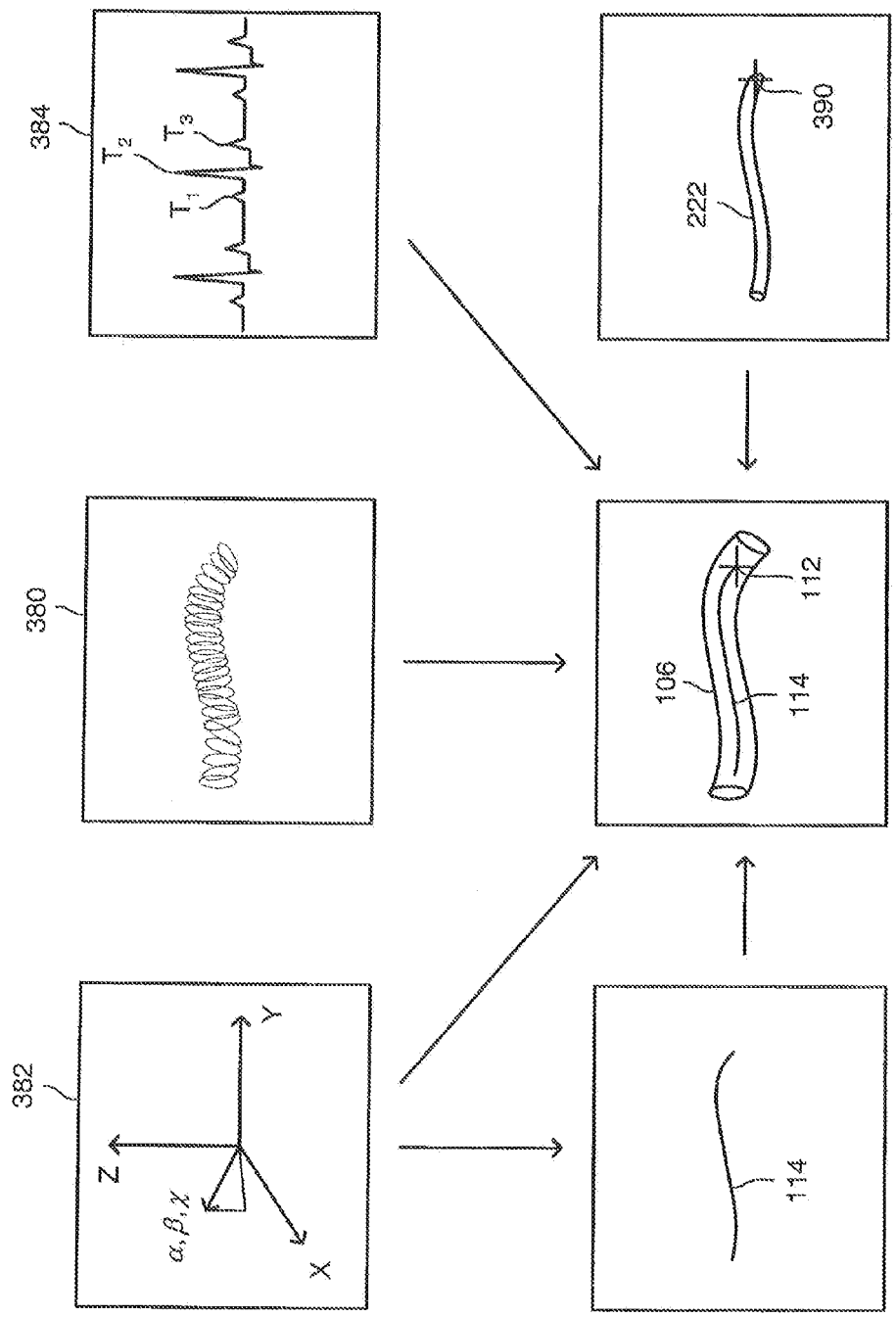
FIG. 11C is a schematic illustration of the process of reconstructing a three-dimensional organ motion dependent image sequence, and superimposing additional visual data thereon, by processing the signals received from the two-dimensional image acquisition device, the MPS and the ECG monitor.

Reference is further made to FIGS. 11A, 11B and 11C. FIG. 11A is a schematic illustration of an ECG of a patient, generally referenced 300. FIG. 11B is a schematic illustration of trajectories of the tip of the catheter of the system of FIG. 6, respective of different activity-states of the ECG of FIG. 11A, constructed according to another embodiment of the disclosed technique. FIG. 11C is a schematic illustration of the process of reconstructing a three-dimensional organ motion dependent image sequence, and superimposing additional visual data thereon, by processing the signals received from the two-dimensional image acquisition device, the MPS and the ECG monitor. The additional visual data can include the position of the catheter within the lumen, the trajectory of a catheter within the lumen, and the like.

ECG 300 includes a plurality of activity-states (e.g. ECG cycle phases), such as activity-states $T_1$, $T_2$ and $T_3$ in each of a plurality of heart cycles 302, 304 and 306. Applicant has found that the position of lumen 108 (FIGS. 1A and 1B) is different at different activity-states, during each of the heart cycles 302, 304 and 306.

For example, at activity-state $T_1$ of each of the heart cycles 302, 304 and 306, the position of lumen 108 is represented by a lumen image at a position 330 (FIG. 11B). At activity-state $T_2$ of each of the heart cycles 302, 304 and 306, the position of lumen 108 is represented by a lumen image at a position 332. At activity-state $T_3$ of each of the heart cycles 302, 304 and 306, the position of lumen 108 is represented by a lumen image at a position 334. At position 330, points 336, 338 and 340 represent different positions of catheter 222 (FIG. 6) at activity-state $T_1$. At position 332, points 342, 344 and 346 represent different positions of catheter 222 at activity-state $T_2$. At position 334, points 348, 350 and 352 represent different positions of catheter 222 at activity-state $T_3$.

Processor 192 (FIG. 6) associates between all of the two-dimensional images (i.e., images acquired at points 336, 338 and 340) which were detected during activity-state $T_1$ at any cycle of ECG signal 300. Similarly, processor 192 associates between all of the two-dimensional images (i.e., images acquired at points 342, 344 and 346) which were detected during activity-state $T_2$ at any cycle of ECG 300 and further associates between all of the two-dimensional images (i.e., images acquired at points 348, 350 and 352) which were detected during activity-state $T_3$ at any cycle of ECG 300.

Processor 192 reconstructs a three-dimensional image from all of the two-dimensional images, which were associated with respect to a given activity-state $T_j$. With reference to FIG. 11B, processor 192 reconstructs three-dimensional image 330, which is the image of the inspected organ at activity-state $T_1$ (FIG. 11A), and three-dimensional image 332, which is the image of the inspected organ at activity-state $T_2$. Likewise, processor 192 reconstructs three-dimensional image 334, which is the image of the inspected organ at activity-state $T_3$.

Processor 192 calculates a trajectory 354 from points 336, 338 and 340, associated with activity-state $T_1$. Similarly, processor 192 calculates a trajectory 356 from points 342, 344 and 346 associated with activity-state $T_2$ and further calculates a trajectory 358 from points 348, 350 and 352 associated with activity-state $T_3$.

Processor 192 associates between each of the calculated trajectories and one of the reconstructed three-dimensional images, respective of a given organ activity-state. With reference to FIG. 11B, processor 192 associates between trajectory 354 and reconstructed three-dimensional image 330, respective of activity-state $T_1$. Similarly, processor 192 associates between trajectory 356 and reconstructed three-dimensional image 332, respective of activity state $T_2$ and further between trajectory 358 and reconstructed three-dimensional image 334, respective of activity-state $T_3$.

Since points 336, 338, 340, 342, 344, 346, 348, 350 and 352, used for calculating the trajectories are also the points at which their respective two-dimensional images were acquired, processor 192 can superimpose each of the calculated trajectories on its respective reconstructed three-dimensional image. For example, processor 192 superimposes trajectory 354 on three-dimensional image 330, trajectory 356 on three-dimensional image 332 and trajectory 358 on three-dimensional image 334.

With reference to FIG. 11C, processor 192 (FIG. 6) reconstructs three-dimensional image 106 (FIG. 1B) of lumen 108, from a plurality of two-dimensional images 380, according to MPS coordinate data 382, all of which are respective of a selected activity-state within the cycles of ECG data 384. Processor 192 reconstructs three-dimensional image 106 from all the two-dimensional images which belong to of activity-state $T_2$. In addition, processor 192 generates trajectory 114 (FIG. 1B) of catheter 222, which corresponds to activity-state $T_2$, from points 342, 344 and 346 (FIG. 11B). Super imposing processor 206 superimposes trajectory 114 and real-time representation 112 (FIG. 1B) of a tip 390 of catheter 222, on three-dimensional image 106.

System 190 (FIG. 6) can playback the sequence of reconstructed images or a selected cycle of the originally acquired two-dimensional images, according to the stored ECG data or at predetermined time intervals. System 190 can also playback the sequence of reconstructed images or a selected cycle of the originally acquired two-dimensional images, in synchrony with real-time detected ECG data.

It is noted that since catheter 222 moves within lumen 108 in real-time, no synchronization is required with respect to the organ timing signal in that aspect. However, it is noted that processor 192 has to register the coordinate system in which the images were acquired, with the coordinate system of the MPS sensor of catheter 222, or to use the same MPS system for the image acquisition process and the playback surgical procedure.

Following is a description of a GUI which allows the operator to freeze a three-dimensional image of a lumen, at a selected activity-state of an organ of the patient. The GUI also allows the operator to move forward and backward in terms of activity-state.

Reference is further made to FIG. 12, which is a schematic illustration of an ECG coordinated display (i.e., a GUI) of a lumen, generally referenced 410, constructed and operative in accordance with a further embodiment of the disclosed technique. ECG coordinated display 410 includes an ECG timing signal 412, a forward button 414, a backward button 416, a freeze button 418 and three-dimensional image 106 (FIG. 1B).

Three-dimensional image 106 corresponds with an activity-state 420 in ECG timing signal 412. When the operator presses forward button 414, a sequence of three-dimensional images of lumen 108 is displayed in a window 422. Each of the three-dimensional images displayed in window 422, corresponds with the respective activity-state in ECG timing signal 412, as if ECG timing signal 412 would advance in a direction designated by an arrow 424.

When the operator presses backward button 416, a sequence of three-dimensional images of lumen 108 is successively displayed in window 422. Each of the three-dimensional images displayed in window 422 corresponds with the respective activity-state in ECG timing signal 412, as if ECG timing signal 412 would retard in a direction designated by an arrow 426.

When the operator presses freeze button 418, a three-dimensional image of lumen 108 is displayed in window 422, wherein the three-dimensional image corresponds with a selected activity-state 428. In this manner the three-dimensional image of lumen 108 in window 422 remains stationary at activity-state 428, during which the physician can inspect the three-dimensional image of lumen 108.

Each of the three-dimensional images, which are displayed in window 422, is acquired by system 190 (FIG. 6), during the scanning process. Thus, the operator can view animated three-dimensional images of lumen 108 as the heart of the patient would beat either forward or backward in time. The operator can alternatively view a three-dimensional image of lumen 108, which corresponds with a selected activity-state during a selected heart cycle of the patient, by pressing freeze button 418 at a selected point in time. It is noted that other sequenced images, such as a reference real-time image (i.e., served as road map during navigation, such as a fluoroscopic image, and the like) can also be made to freeze-up.

Following is a description of a GUI for identifying a plaque within the lumen, having a selected percentage of occlusion. According to an algorithm, the processor automatically designates the necessary marks on a real-time image of the lumen, as the selected position to which the stent is to be delivered.

Figure 13A:
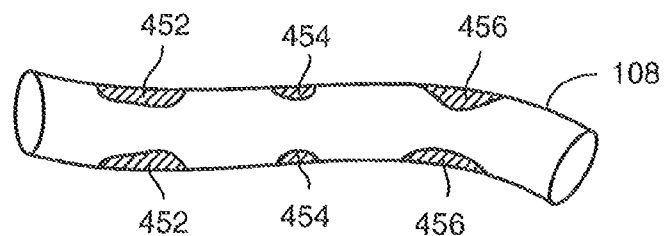
FIG. 13A is an illustration of the lumen of FIG. 1A, having a plurality of occluded regions.
Figure 13B:
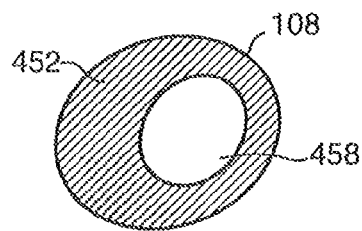
FIG. 13B is a cross-sectional view of a selected region of the lumen of FIG. 13A.
Figure 13C:
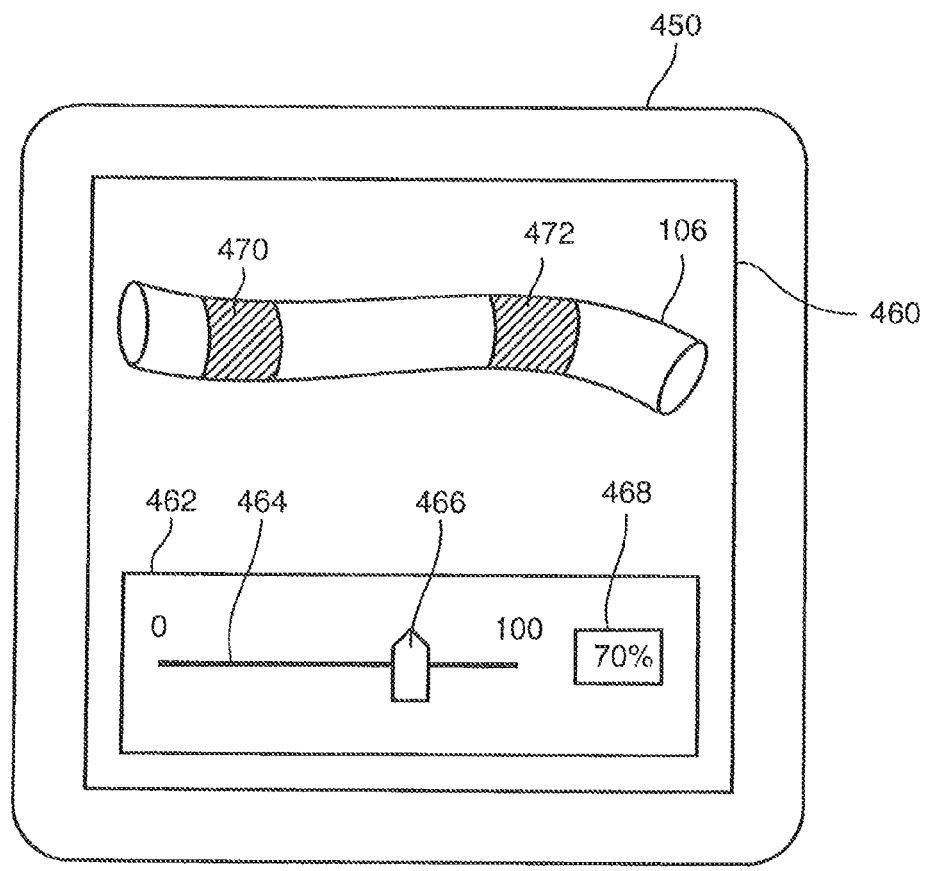
FIG. 13C is a schematic illustration of a representation of the lumen of FIG. 13B in a GUI, operative in accordance with another embodiment of the disclosed technique.

Reference is further made to FIGS. 13A, 13B and 13C. FIG. 13A is an illustration of the lumen of FIG. 1A, having a plurality of occluded regions. FIG. 13B is a cross-sectional view of a selected region of the lumen of FIG. 13A. FIG. 13C is a schematic illustration of a representation of the lumen of FIG. 13B in a GUI, generally referenced 450, operative in accordance with another embodiment of the disclosed technique.

Lumen 108 includes plaques 452, 454 and 456. It is noted that plaques 452, 454 and 456 can be fixed in their places or be dynamic. Plaques 452, 454 and 456 block lumen 108 by 75%, 60% and 80%, respectively. With reference to FIG. 13B, the hatched area denotes the blockage due to plaque 452 within lumen 108, leaving ducting 458 open for blood flow.

Processor 190 (FIG. 6) can determine the percentage of occlusion, according to a plurality of methods, taking into account parameters such as plaque type, plaque density, and the like. The following is a simple example for such a method:

$$\%_{BLOCKED} = \left(1 - \frac{S_{LUMEN}}{S_{ARTERY}}\right) \cdot 100$$

where, $S_{LUMEN}$ denotes the cross section of ducting 458 and $S_{ARTERY}$ denotes the total internal area of lumen 108.

GUI 450 includes a graphical window 460. Graphical window 460 includes three-dimensional image 106 and a ratio selection window 462. Ratio selection window 462 includes a graduation bar 464, a pointer 466 and a numerical box 468. The operator can dynamically set the occlusion percentage threshold, by dragging pointer 466 along graduation bar 464, via user interface 208 (FIG. 6). Alternatively, the operator can enter a selected occlusion percentage threshold in numerical box 468, through user interface 208. In the example set forth in FIG. 13B, the numerical value 70%, of the selected percentage is shown in numerical box 468.

System 190 (FIG. 6) then marks only those regions on three-dimensional image 106, which are occluded more than the selected occlusion percentage. In the example set forth in FIG. 13B, only those regions of lumen 108 which are occluded 70% or more, are marked in three-dimensional image 106. Plaques 452 and 456, which exceed 70%, are represented by marked regions 470 and 472, respectively, on three-dimensional image 106. Marked regions 470 and 472 are differentiated from the rest of the portions of three-dimensional image 106, by being colored in a different hue, marked by hatches, animated, and the like.

It is noted the system enables the operator to manually correct the marking on screen, in case that the operator, according to her medical knowledge and experience detects for example, that the plaque portion should be different than what the system indicated. It is further noted that the system can present the various layers of the lumen (i.e., media, adventitia and intima), in GUI 450, in different colors.

Following is a description of a method for detecting the organ timing signal of the lumen, either due to the cardiac cycle or the respiratory cycle, by employing the MPS, instead of the ECG monitor. The term "time-tagging" herein below refers to the process of associating a data element, with the exact time at which that data element was obtained (e.g., associating an MPS coordinate reading with the exact time at which that reading was obtained). The data obtained via each of MPS sensors $210_1$, $210_2$, $210_3$ and $210_N$ is time-tagged. The two-dimensional images acquired by each of two-dimensional image acquisition devices 194 is also time-tagged. The time-tags are taken into account when processing the data elements stored in adaptive volumetric database 204.

Latency compensation is performed on all the time-tagged data elements. In general, image frames from the set of two-dimensional (2D) images acquired by two-dimensional image acquisition devices 194 are shifted so that the time-tags thereof match the time-tag of the corresponding MPS data set (i.e., images acquired at the same time as an MPS coordinate reading was obtained will be matched with one another).

The term "corresponding data sets" herein below, refers to a pair of data sets which have the same time-tags. It is noted that the time-tag of a data set refers to the set of time-tags of the elements within the data set. For example, an MPS data set is corresponding with a two-dimensional images data set if readings in the MPS data set have the same time-tag as the images in the two-dimensional images data set.

Corresponding data sets represent data sets that occur during the same session in a medical procedure. The term "Non-corresponding data sets" herein below, refers to a pair of data sets which have different time-tags. For example, an MPS data set is non-corresponding with a two-dimensional images data set if the readings in the MPS data set have a different time-tag than all the images in the two-dimensional images data set. Non-corresponding data sets represent data sets that were recorded during different sessions (within the same or different medical procedures).

Figure 14:
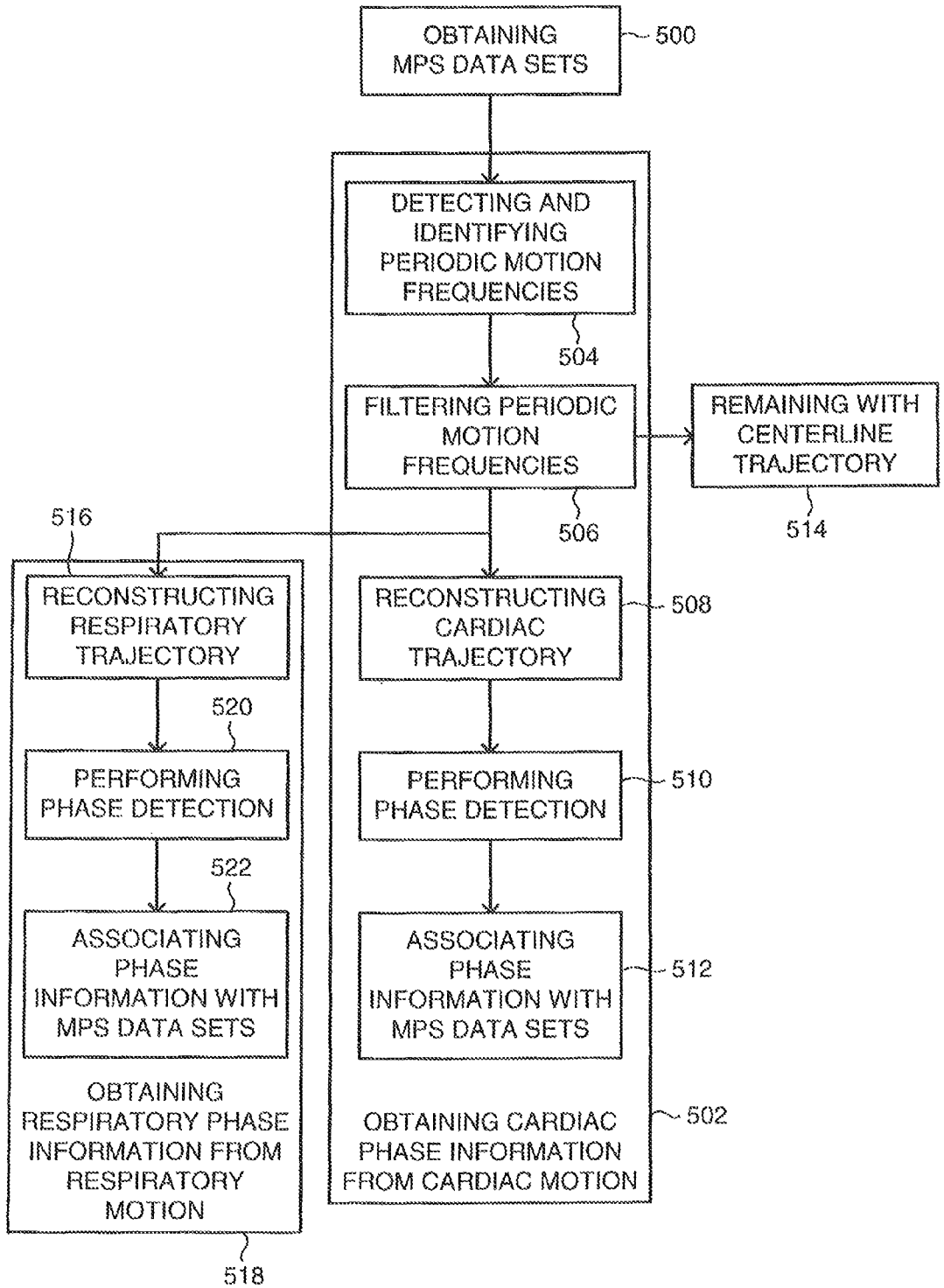
FIG. 14 is a schematic illustration of a method for determining an organ timing signal of an organ of the patient, according to position data of an MPS sensor which moves together with the movements of the organ, operative in accordance with a further embodiment of the disclosed technique.

Reference is further made to FIG. 14, which is a schematic illustration of a method for determining an organ timing signal of an organ of the patient, according to position data of an MPS sensor which moves together with the movements of the organ, operative in accordance with a further embodiment of the disclosed technique. In procedure 500, data sets are obtained from MPS 198 (FIG. 6). Each data set includes a series of position coordinate readings of two-dimensional image acquisition device 164, catheter 222, a selected area of the body of patient 216, or the operating table on which patient 216 is lying, respectively, as received from one of plurality of MPS sensors $210_1$, $210_2$, $210_3$ and $210_N$.

MPS 198 processes detected electromagnetic fields to obtain the respective position coordinate readings, which are subsequently stored in adaptive volumetric database 204. It is recalled that each MPS sensor position coordinate reading is time-tagged, or associated with the exact time at which the reading was obtained. Thus, each MPS data set received from MPS sensor $210_1$ includes a collection of coordinate readings demonstrating the precise motion trajectory of catheter 222 over time.

In procedure 502, cardiac phase information is obtained from cardiac motion. In particular, cardiac phase information is obtained from data streams originating from MPS sensor $210_1$ located on catheter 222. Procedure 502 consists of procedures 504, 506, 508, 510 and 512.

In procedure 504, periodic motion frequencies are detected and identified in a time-tagged MPS data set. As catheter 222 is maneuvered within lumen 108, the motion of catheter 222 is influenced by two additional factors. The first factor relates to the activity of the heart, or cardiac motion, such as systole and diastole. Cardiac motion affects lumen 108 in a certain way, such as contraction or expansion in varying degrees and at periodic intervals. The second factor relates to the breathing activity, or respiratory motion, such as inhaling and exhaling. Respiratory motion affects lumen 108 in a certain way, such as contraction or expansion in varying degrees and at periodic intervals. Taken together, the overall motion of catheter 222 is composed of the cardiac motion and the respiratory motion superimposed onto the movement associated with maneuvering catheter 222 (which corresponds to the topography of the lumen system).

Since the cardiac motion and respiratory motion are cyclic in nature, the periodic frequencies can be detected in the overall trajectory of catheter 222. The specific frequencies relating to the cardiac motion exhibit different characteristics than the specific frequencies relating to the respiratory motion. The specific frequencies relating to the cardiac motion are identified from the detected periodic frequencies. Similarly, the specific frequencies relating to the respiratory motion are identified from the detected periodic frequencies. Processor 192 performs the analysis on the MPS data set and identifies the relevant periodic motion frequencies.

In procedure 506, periodic motion frequencies are filtered from the time-tagged MPS data set. The periodic motion frequencies detected in procedure 504 are separated out from the overall trajectory of catheter 222. The remaining motion components correspond to the central axis of the maneuvers of catheter 222, which represents the vessel topography, or "centerline trajectory" (referenced procedure 514). The time-tags associated with the MPS data set are retained for each of the filtered periodic motion frequencies. Processor 192 filters out the relevant periodic motion frequencies from the MPS data set.

In procedure 508, the mechanical movement of lumen 108 due to the cardiac motion, or "cardiac trajectory", is reconstructed from the MPS data sets and from the filtered periodic motion frequencies. In particular, the cardiac trajectory is reconstructed according to the previously identified specific frequencies relating to the cardiac motion. The reconstructed cardiac trajectory may be reflected, for example, by a graph that indicates the trajectory of lumen 108 due to cardiac motion over a period of time. Processor 192 analyzes the relevant periodic motion frequencies and creates a reconstruction of the cardiac trajectory.

In procedure 516, the mechanical movement of lumen 108 due to the respiratory motion, or "respiratory trajectory", is reconstructed from the MPS data sets and the filtered periodic motion frequencies. In particular, the respiratory trajectory is reconstructed according to the previously identified specific frequencies relating to the respiratory motion. The reconstructed respiratory trajectory may be reflected, for example, by a graph that indicates the trajectory of lumen 108 due to respiratory motion over a period of time. Processor 192 analyzes the relevant periodic motion frequencies and creates a reconstruction of the respiratory trajectory.

Reconstruction of the respiratory trajectory may be based solely on coordinate readings obtained from the external reference sensors (i.e., MPS sensors $210_N$ or $210_3$). It is noted that an additional reference sensor (or plurality thereof) may be attached (i.e., externally or internally) to the body of patient 216, to monitor breathing patterns, and the like. For example, an intravascular sensor may be used for this purpose.

This sensor functions as a confirmation mechanism to provide supporting data regarding respiratory motion, and more accurately determine periodic motion frequencies relating to respiratory motion. It is noted that the same or an additional sensor (or plurality thereof) may be used for gathering additional cardiac data either as a confirmation mechanism or for providing supporting data for cardiac phase detection.

In procedure 510, phase detection is performed on the reconstructed cardiac trajectory. The cardiac trajectory consists of different phases or activity-states of the heart, corresponding to different points within a cardiac cycle. The phases repeat themselves periodically with each cycle. The plurality of cardiac activity-states is identified on the reconstructed cardiac trajectory during phase detection. Processor 192 performs the analysis of the cardiac trajectory and identifies the different cardiac cycle phases.

Figure 15A:
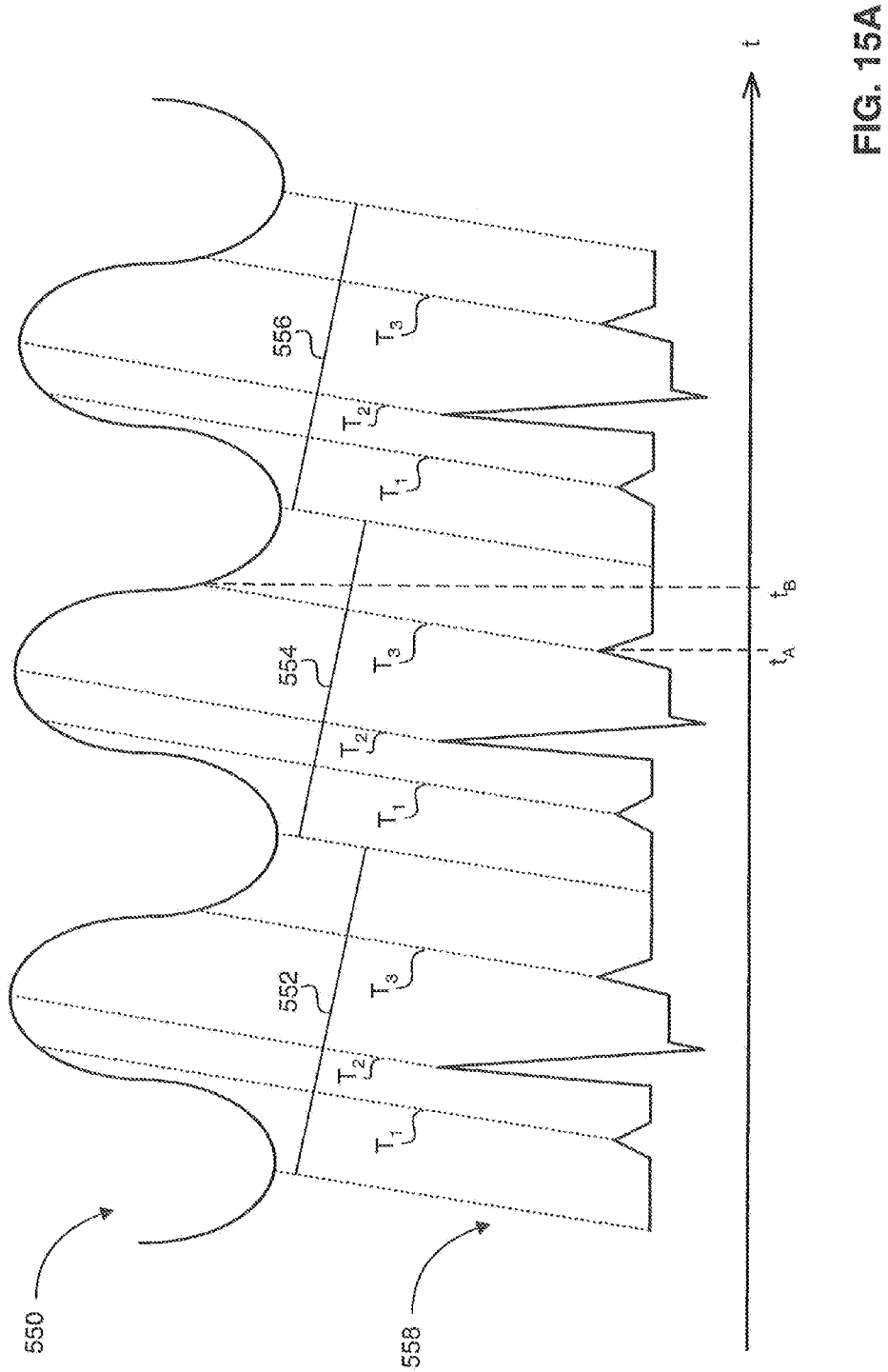
FIG. 15A is a schematic illustration of a cardiac trajectory, in an electrical signal representation and in a mechanical signal representation.

Reference is further made to FIG. 15A, which is a schematic illustration of a cardiac trajectory, in an electrical signal representation and in a mechanical signal representation. The mechanical signal representation of the cardiac trajectory, generally referenced 550, includes a plurality of cardiac activity-states (i.e., cardiac cycle phases), such as activity-states $T_1$, $T_2$ and $T_3$, in each of a plurality of cardiac cycles 552, 554 and 556. The mechanical representation of the cardiac trajectory is equivalent to the cardiac trajectory reconstructed from the MPS data sets and the filtered periodic motion frequencies (procedures 506 and 508). The electrical signal representation of the cardiac trajectory, generally referenced 558, depicts the same activity-states $T_1$, $T_2$ and $T_3$, in each of cardiac cycles 552, 554 and 556.

However the precise time at which these activity-states occur may be different in the two representations, as there is a slight delay at the electrical representation with respect to the mechanical representation. For example, it is shown that activity-state $T_3$ of cardiac cycle 554 occurs a at time $t_A$ in cardiac trajectory 550 and at a time $t_B$ in cardiac trajectory 558. Therefore, it is necessary to perform an alignment between the activity-states, when using information from the electrical representation for phase detection. The electrical representation 558 of the cardiac trajectory is equivalent to the electrical timing signals obtained by ECG monitor 196.

It is noted that the detection of cardiac phases is performed based solely on data sets originating from at least MPS sensor $210_1$ located on catheter 222, and perhaps also from the reference sensors (i.e., MPS sensors $210_3$ and $210_N$). These data sets provide a mechanical representation of the cardiac trajectory. No external monitoring device is required to obtain cardiac phase information.

It is noted that periodic motion components relating to the respiratory motion may also be used as supporting data for cardiac phase detection. It is further noted that phase detection may be performed on the original MPS data sets, rather than on the reconstructed cardiac trajectory, using the detected and filtered periodic motion frequencies. The different phases or activity-states of the heart are identified directly on the MPS data sets obtained in procedure 500.

In procedure 512, cardiac phase information is associated with the MPS data sets. Each data set obtained from MPS sensor $210_1$ relating to the position of catheter 222 is matched to one of a plurality of activity-states $T_1$, $T_2$ and $T_3$, according to their corresponding time elements (i.e., time-tags). The position of lumen 108, and consequently the position of catheter 222, is different during different activity-states of lumen 108. Processor 192 associates between a coordinate reading and the matching phase thereof, and stores the information in adaptive volumetric database 204.

Respiratory phase information may be obtained from the respiratory motion, in a similar manner as cardiac phase information is obtained from the cardiac motion. Respiration activity-states may be identified on the reconstructed respiratory trajectory using the periodic motion components relating to the respiratory motion. Periodic motion components relating to the respiratory motion may also be used in correlation with non-corresponding data sets.

Respiratory phase information is obtained from respiratory motion in an optional procedure 518. Procedure 518 consists of procedures 516, 520 and 522. In procedure 516, a respiratory trajectory is reconstructed from the MPS data sets and the filtered periodic motion frequencies, as described herein above in connection with procedures 504, 506 and 508.

In procedure 520, phase detection is performed on the reconstructed respiratory trajectory. Like the cardiac trajectory, the respiratory trajectory consists of different phases or activity-states of the lungs, corresponding to different points within a respiratory cycle. The respiratory activity-states of the lungs can be identified from the phases of the respiratory trajectory. The phases repeat themselves periodically with each cycle. The respiratory activity-states are identified on the reconstructed respiratory trajectory during phase detection.

Processor 192 performs the analysis of the respiratory trajectory and identifies the different respiratory cycle phases.

Reference is further made to FIG. 15B, which is a schematic illustration of a respiratory trajectory in a mechanical signal representation, generally referenced 560. Mechanical signal representation 560 includes a plurality of respiratory activity-states (i.e., respiratory cycle phases), such as activity-states $T_4$, $T_5$ and $T_6$. Mechanical representation 560 is equivalent to the respiratory trajectory reconstructed from the MPS data sets, and the filtered periodic motion frequencies in procedure 508.

It is noted that the detection of respiratory phases is performed based solely on data sets detected by MPS sensor $210_1$ located on catheter 222, and from MPS sensors $210_N$ and $210_3$, attached to the body of patient 216, and the operation table, respectively. These data sets provide a mechanical representation of the respiratory trajectory. No external monitoring device is required to obtain respiratory phase information. It is further noted that phase detection may be performed on the original MPS data sets, rather than on the reconstructed respiratory trajectory, using the detected and filtered periodic motion frequencies. The different phases or activity-states of the lungs are identified directly on the MPS data sets obtained in procedure 500.

It is noted that the actual value of the cardiac rate or respiratory rate of the patient may be obtained without using any external monitoring device (such as ECG monitor 196). The cardiac rate or respiratory rate of patient 216 can be obtained solely from MPS sensors $210_1$, $210_3$ and $210_N$, either individually or jointly.

In procedure 522, respiratory phase information is associated with the MPS data sets. Each data set obtained from MPS sensor $210_1$ relating to position of catheter 222 is matched to one of activity-states $T_4$, $T_5$ and $T_6$, according to their corresponding time-tags. Procedure 522 is analogous to procedure 512 discussed herein above.

Following is a description of automatic maneuvering of catheter 222 (FIG. 6) within lumen 108 (FIG. 1A). The term "topological representation" herein below, refers to a mapping of a lumen system (e.g., the circulation, the bronchial tree, the urogenital system, the renal system) of the body of the patient, which a system according to the disclosed technique employs, in order to maneuver the catheter from an origin to a destination. The mapping can be either two-dimensional or three-dimensional. Alternatively, it is noted that the term "topological representation" may include just the path to be followed in the lumen system.

Figure 16:
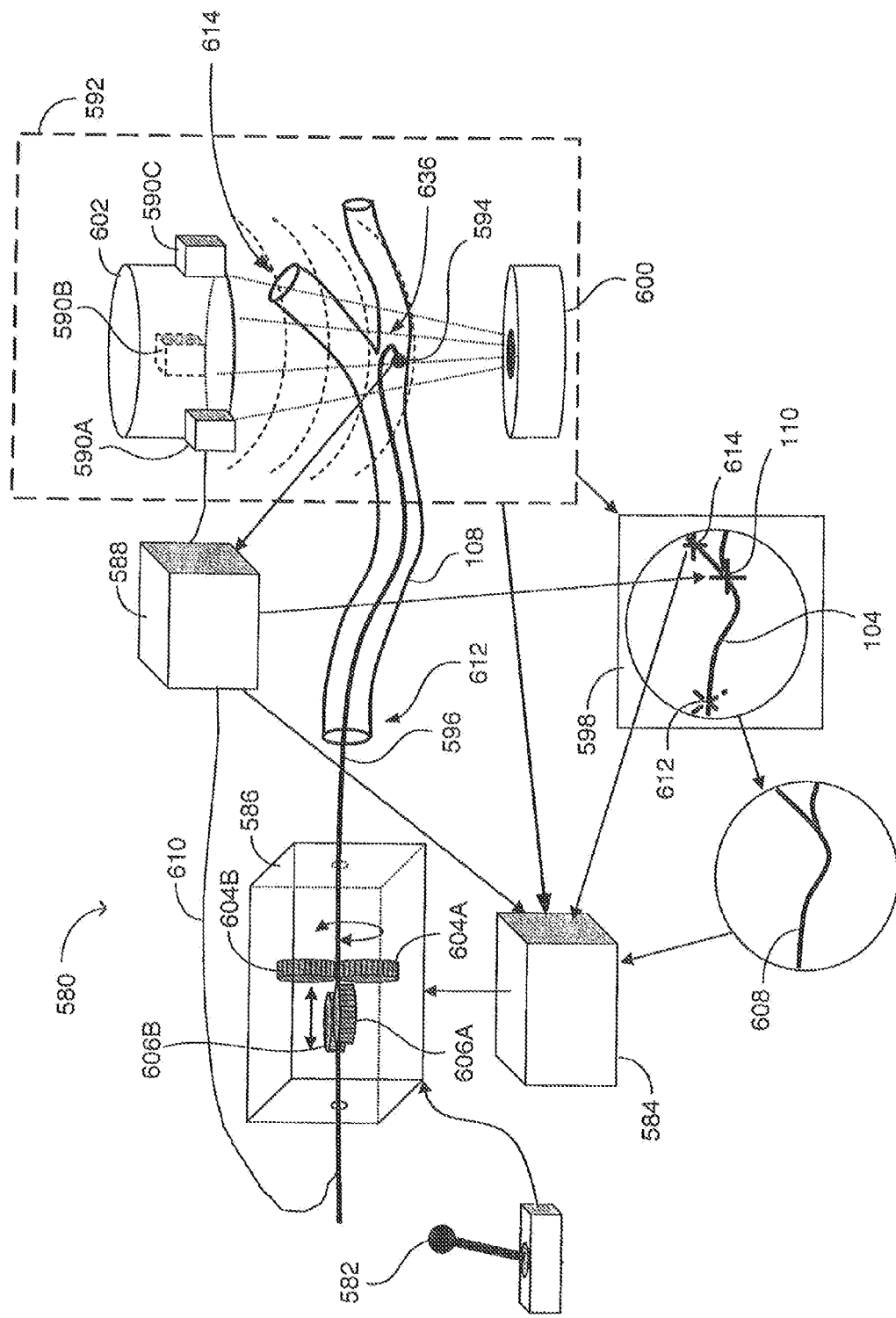
FIG. 16 is a schematic illustration of a system for automatically maneuvering a catheter within a lumen of the body of a patient, constructed and operative in accordance with another embodiment of the disclosed technique.
Figure 17:
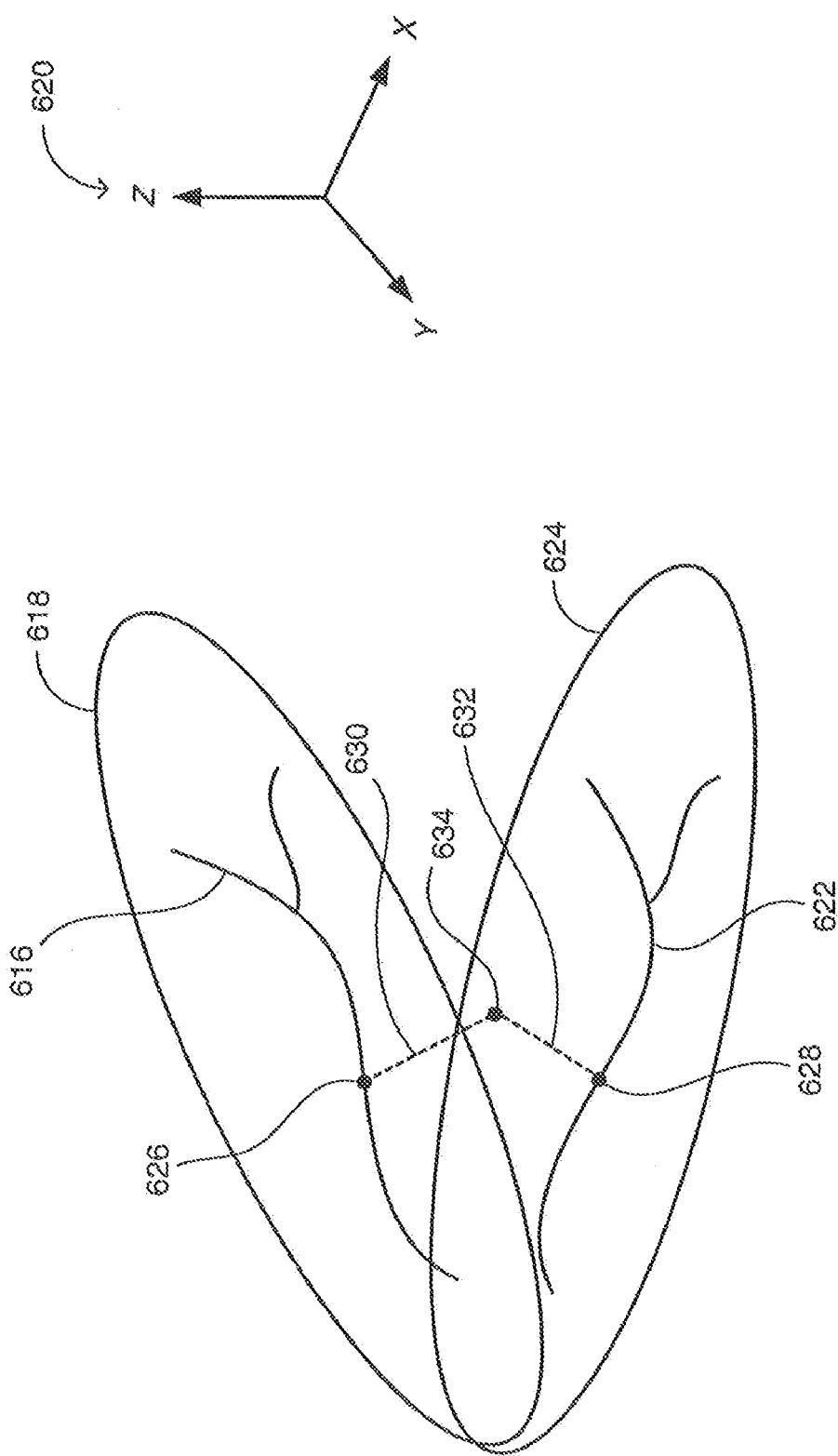
FIG. 17 is a schematic illustration of a method by which the imaging system of the system of FIG. 16 determines the coordinates of a path within the lumen, in three dimensions.

Reference is further made to FIGS. 16 and 17. FIG. 16 is a schematic illustration of a system, generally referenced 580, for automatically maneuvering a catheter within a lumen of the body of a patient, constructed and operative in accordance with another embodiment of the disclosed technique. FIG. 17 is a schematic illustration of a method by which the imaging system of the system of FIG. 16 determines the coordinates of a path within the lumen, in three dimensions.

With reference to FIG. 16, system 580 includes a joystick 582, a controller 584, a moving mechanism 586, an MPS 588, a plurality of transmitters 590A, 590B and 590C, an imaging system 592, a position detector 594, a catheter 596 and a display 598. Imaging system 592 includes a radiation generator 600 and a radiation detector 602. Imaging system 592 can be an X-ray system, fluoroscope, C-arm imager, CT, PET, ultrasound system, MRI, and the like.

Moving mechanism 586 can include a pair of angular movement rollers 604A and 604B, and a pair of linear movement rollers 606A and 606B, and respective moving elements (not shown) such as electric motors, actuators, and the like. However, moving mechanism 586 can include other, alternative or additional elements, as long as it imparts to catheter 596 the necessary motions described herein below (e.g., piezoelectric motors which transfer linear movement through friction). Optionally, moving mechanism 586 can be disposable in order to keep it sterile. Controller 584 includes a processor (not shown) and a storage unit (not shown) for storing information respective of a path 608, which catheter 596 should move according to, within lumen 108 (FIG. 1A).

Moving mechanism 586 is coupled with joystick 582 and with controller 584. Controller 584 is coupled with imaging system 592. MPS 588 is coupled with controller 584 and with transmitters 590A, 590B and 590C. Position detector 594 is coupled with MPS 588 by a conductor 610 (i.e., a conductive coupling). Display 598 is coupled with MPS 588 and with imaging system 592. Position detector 594 is located at a distal portion of catheter 596.

Controller 584, MPS 588, imaging system 592, display 598, position detector 594, and each of transmitters 590A, 590B and 590C, are similar to processor 192 (FIG. 6), MPS 198, two-dimensional image acquisition devices 194, display 214, MPS sensor $210_1$, and transmitter 212, respectively. Hence, the moving mechanism can be incorporated with the system of FIG. 6, and coupled with the processor, the MPS, and the catheter of FIG. 6.

During the medical operation, the body of the patient (not shown) is located between radiation generator 600 and radiation detector 602. Imaging system 592 has at least one degree of freedom, thereby being able to take a plurality of images of the body of the patient, from different directions. Imaging system 592 provides a signal to display 598, respective of two-dimensional image 104 (FIG. 1A), for display 598 to display two-dimensional image 104.

Path 608 is a three-dimensional curve between an origin 612 and a destination 614 of a distal portion (not shown) of catheter 596 relative to lumen 108. Both origin 612 and destination 614 are within a field of view of imaging system 592. Path 608 is determined during an imaging session prior to the medical operation, and stored in the storage unit.

Controller 584 calculates and constructs path 608, for example, according to a plurality of two-dimensional images obtained from lumen 108, with the aid of a C-arm imager. For example, the C-arm can obtain two two-dimensional ECG gated images of lumen 108 at two different non-parallel ECG gated image planes. When the operator indicates origin 612 and destination 614, the C-arm constructs path 608 in three dimensions. It is noted that controller 584 calculates path 608 based on one or more image processing algorithms, according to contrast variations of lumen 108 relative to the background.

With further reference to FIG. 17, imaging system 592 captures an image 616 of lumen 108 on an image plane 618 in a three-dimensional coordinate system 620, and another image 622 of lumen 108 on an image plane 624 in three-dimensional coordinate system 620. Imaging system 592 is aware of the orientation between image planes 618 and 624 (i.e., the angles there between). Imaging system 592 identifies a feature 626 of lumen 108 in image 616 and a corresponding feature 628 in image 622. Imaging system 592 determines the three-dimensional coordinates of feature 626 (or feature 628) in three-dimensional coordinate system 620, by determining the intersection of normals 630 and 632 from features 626 and 628, respectively, to image planes 618 and 624, respectively, at a point 634. Imaging system 592 performs the above procedure for other features of lumen 108, thereby constructing path 608 in three dimensions.

A two-dimensional image which the C-arm obtains from the body of the patient, can include other lumens (not shown)

in addition to lumen 108, which are located at planes different than the plane of lumen 108 (i.e., these additional lumens overlap lumen 108 in the captured image). In this case, when the operator indicates origin 612 and destination 614, it is not evident to the C-arm that the operator is interested in a path through lumen 108, and the C-arm can construct a path (not shown), which passes through another lumen which in the two-dimensional image overlaps lumen 108. Hence, the C-arm obtains another two-dimensional image of lumen 108 at another image plane, such that in the new two-dimensional image, lumen 108 is not overlapped by any other lumens.

Prior to the medical operation, the coordinate systems of MPS 588 and imaging system 592 are set to a common two-dimensional coordinate system, for display 598 to superimpose real-time representation 110 (FIG. 1A) of position detector 594, on two-dimensional image 104, during the medical operation. This method is described herein above in connection with FIG. 11C. The information displayed by display 598, serves the physical staff to observe the location of the distal portion of catheter 596 relative to lumen 108, throughout the medical operation. This two-dimensional coordinate system can be determined for example, according to the following method.

A first transformation model between the three-dimensional coordinate system of MPS 588 and the three-dimensional coordinate system of imaging system 592 is determined. A second transformation model between the three-dimensional coordinate system of imaging system 592 and a two-dimensional coordinate system of imaging system 592 is determined. The three-dimensional coordinate system of MPS 588 is transformed to the three-dimensional coordinate system of imaging system 592, by applying the first transformation model to the three-dimensional coordinate system of MPS 588. The three-dimensional transformed coordinate system of imaging system 592 is transformed to the two-dimensional coordinate system of imaging system 592, by applying the second transformation model to the three-dimensional transformed coordinate system of imaging system 592.

The first transformation model is determined according to a set of points in the three-dimensional coordinate system of MPS 588 and another set of points in the three-dimensional coordinate system of imaging system 592. The second transformation model is determined according to external parameters of imaging system 592 (i.e., a set of points in the three-dimensional coordinate system of imaging system 592) and internal parameters of imaging system 592 (e.g., lens angle, focal length, magnification).

Following is a description of operation of system 580, for performing an operation on the vessels in the neck region of patient 216 (FIG. 6). In this case, path 608 is a three-dimensional curve within the axillary artery (represented by lumen 108) which marks a path from the region of the first rib (i.e., origin 612) to the thyrocervical trunk (i.e., destination 614). At the stage of medical operation, the physical staff inserts catheter 596 to the body of the patient through the right brachial artery (not shown), and manually maneuvers catheter 596 to reach origin 612.

At this point, system 580 takes over, to automatically maneuver catheter 596 to destination 614. In response to the electromagnetic field produced by transmitters 590A, 590B and 590C, position detector 594 sends a signal to MPS 588 via conductor 610, respective of the three-dimensional position of position detector 594. Alternatively, position detector 594 is coupled with MPS 588 wirelessly and without conductor 610, in which case position detector 594 sends this position signal to MPS 588 wirelessly.

MPS 588 determines the coordinates of position detector 594 according to the signal received from position detector 594. MPS 588 sends a signal respective of the coordinates of position detector 594 to controller 584, in the three-dimensional coordinate system of MPS 588. MPS 588 sends a signal respective of the coordinates of position detector 594 to display 598, in the two-dimensional coordinate system of imaging system 592, as described herein above.

Throughout the medical operation, display 598 displays two-dimensional image 104 of an operational region of lumen 108 (i.e., a section between origin 612 and destination 614) according to a signal received from imaging system 592. Display 598 also displays representation 110 of the current location of position detector 594 (i.e., the distal portion of catheter 596), superposed on two-dimensional image 104, according to the signal received from MPS 588. Alternatively, the current location of the position detector can be superposed on a three-dimensional image of the lumen (e.g., the coronary tree).

Instead of path 608, the controller can employ a topographical representation of the lumen system of patient 216, in order to control the moving mechanism to maneuver the catheter through the lumen system, from an origin to a destination within the lumen system. In this case, the controller determines the best path for the catheter to reach the destination. It is noted that the controller may change the path in real-time, depending on findings during the navigation process (e.g., blocked passages, lumen which is narrower than expected). The controller modifies the path according to the feedback provided in real time by the position detector, and by comparing the actual position and orientation of the position detector with the expected position and orientation. Furthermore, the controller modifies a predefined three-dimensional path which is used as a three-dimensional roadmap for the planning process.

The system can further include a processor (not shown) coupled with the MPS and with the display, and an organ monitor (not shown) such as an ECG coupled with the processor, as described herein above in connection with FIG. 6. The Organ monitor monitors the organ timing signal of a monitored organ and sends a respective signal to the processor. The processor sends a video signal to the display respective of an image of the lumen, corresponding with the current activity-state of the monitored organ detected by the organ monitor. The Display displays an image of the lumen, according to the current activity-state. Thus, the display displays a superposition of a representation of the position detector on a reconstructed image of the lumen, taking into account the movements of the lumen due to the timing signal of the monitored organ (e.g., the heart beat of the patient). The display can display a three-dimensional reconstructed image of the lumen, as described herein above in connection with FIG. 6. This three-dimensional reconstructed image is displayed relative to the coordinate system of the body of the patient.

Alternatively, the medical positioning system can filter out the organ timing signal (i.e., producing a filtered MPS reading) and the current position of the position detector in the coordinate system of the lumen, from a multitude of positions of the position detector, in the coordinate system of the body of the patient. In this case, the controller updates the topological representation and the position of the tip of the catheter according to the filtered MPS reading. The controller controls the moving mechanism according to the updated topological representation and the updated position of the catheter. Furthermore, the display can display the updated topological representation and the updated representation of the distal portion of the catheter, superposed on a substantially stationary three-dimensional reconstructed image of the lumen.

Moving mechanism 586 operates according to the commands received from controller 584, to maneuver catheter 596 along path 608, from origin 612 to destination 614. For this purpose, the pair of angular movement rollers 604A and 604B twist catheter 596 clockwise and counterclockwise relative to the longitudinal axis (not shown) of catheter 596, and the pair of linear movement rollers 606A and 606B move catheter 596 forward and backward. Controller 584 constantly receives a signal from MPS 588 respective of three-dimensional coordinates of position detector 594 at any given time (i.e., a feedback), thereby allowing moving mechanism 586 to apply corrections to possible errors of movement along path 608. These corrections are applied in the following manner.

Controller 584 sends a signal at predetermined time increments to moving mechanism 586, to advance catheter 596 by a predetermined displacement increment. Controller 584 determines the advancement of the distal portion of catheter 596 at each time increment (according to the position signal received from MPS 588), and checks whether this advancement substantially matches the predetermined displacement by which catheter 596 was supposed to advance. In case the actual detected advancement does not match the predetermined displacement increment, controller 584 determines that catheter 596 has made contact with an obstacle (not shown) which prevents catheter 596 to advance according to path 608 (e.g., the distal portion of catheter 596 can be stuck at a bifurcation 636).

In this case, controller 584 sends a signal to moving mechanism 586 to retreat catheter 596 by a selected increment backward within lumen 108, and also to twist the distal portion of catheter 596 by a selected amount. After this twist, controller 584 sends a signal to moving mechanism 586 to advance catheter 596 by a predetermined displacement increment. Thus, moving mechanism 586 can maneuver catheter 596 to overcome the obstacle and to enter the predetermined branch (in this case the thyrocervical trunk at bifurcation 636).

It is noted that due to the three-dimensional position information which controller 584 receives as a real time feedback from MPS 588, controller 584 can control the operation of moving mechanism 586 to maneuver catheter 596 in three-dimensions. Thus, system 580 provides an advantage over systems in the prior art, in which the physical staff can maneuver the catheter according to a two-dimensional display, only in two dimensions. System 580 provides automatic maneuvering of catheter 596 through lumen 108 in three dimensions, while performing feedback oriented real time corrections in order to reach destination 614 within lumen 108.

Imaging system 592 (e.g., a C-arm) can detect lumen 108 from different directions in order to provide the information necessary for display 598 to display two-dimensional image 104. Imaging system 592 selects the one specific imaging direction at which the average distance of path 608 from an image plane (not shown), is minimal. If $X_i$ is the distance from a point i on path 608 normal to the image plane, where i=1, 2, 3 . . . N, then the minimum average distance is, $$\min \frac{\sum_{1}^{N} X_i}{N} \quad (1)$$

In case path 608 follows many curves in space and deviates significantly from a two-dimensional path, then imaging system 592 can divide path 608 to different parts, and prepare the information for two-dimensional image 104, by selecting a different image plane for each part, while satisfying Equation 1.

It is noted that more than one position detector can be located at the distal portion of the catheter. This arrangement is crucial in case the distal portion of the catheter is provided with a "curve-back" functionality. The "curve-back" movement can be provided for example, by employing Electro Active Polymers (EAP). The moving mechanism is likewise provided with the necessary elements to apply an appropriate torque to the distal portion of the catheter, to bend the distal portion. Moreover, with the aid of multiple position detectors, the display can display the current geometry of the distal portion.

Furthermore, the controller can obtain a more complete information respective of the geometry of the distal portion of the catheter, when the catheter is blocked by an obstacle, and thus expedite the maneuvering operation. For example, if the controller detects that the distal portion of the catheter has unexpectedly bent, then the controller determines that the tip of the catheter has made contact with an obstacle in the lumen. The controller can reach this conclusion for example, by comparing the detected orientation of the position detector at a given point within the lumen, with the computed slope of the path at the same point within the lumen. In case the detected orientation and the computed slope do not match, the controller determines that the catheter has met an obstacle, thereby directing the moving mechanism to operate in order to move the catheter back from the obstacle.

In case the physical staff is unsatisfied with the automatic operation of moving mechanism 586, he can override controller 584, and manually operate moving mechanism 586 via joystick 582. The operator can intervene in any phase of operation of system 580, using joystick 582. This is a semi-automatic mode of operation of system 580, wherein controller 584 enables moving mechanism 586 to maneuver catheter 596 through the trivial portions of path 608, and the operator takes control of system 580 in the more intricate portions of path 608. In case of manual intervention, joystick 582 overcomes any automated action. It is noted that both in the automatic mode and the manual mode, the operator receives a visual feedback of the advancement of catheter 596 within lumen 108, by viewing representation 110 of the tip of catheter 596 on display 598.

It will be appreciated by persons skilled in the art that the disclosed technique is not limited to what has been particularly shown and described hereinabove. Rather the scope of the disclosed technique is defined only by the claims, which follow.

The invention claimed is:

1. A system for delivering a stent coupled with a catheter to a selected position within a lumen of the body of a patient, comprising:
 a medical positioning system (MPS) for determining a current position of said stent within said lumen, in a coordinate system respective of said MPS, according to position data acquired by an MPS sensor attached to said catheter in the vicinity of said stent;
 a user interface configured to allow a user to select an occlusion percentage threshold;
 a processor coupled with said user interface and with said MPS, said processor configured to determine said selected position in said lumen to which said stent is to be delivered by identifying a region of said lumen that is occluded more than said selected occlusion percentage threshold, said processor being further configured to designate said identified region on an image of said lumen with at least one mark;

said MPS being further configured to repeatedly determine said current position while said catheter is being maneuvered within said lumen, said processor being configured to superimpose a stent representation respective of said determined current position on said image;

said processor being further configured to produce an output when said current position, represented by said stent representation in said image, is substantially aligned with said selected position, represented by said mark in said image.

2. The system of claim 1 wherein said user interface has (i) a graphical window that includes said image of said lumen and (ii) a ratio selection window configured to allow said user to select said occlusion percentage threshold.

3. The system of claim 2 wherein said ratio selection window includes a graduation bar and a pointer, said pointer being configured to be dragged by said user along said graduation bar to set said occlusion percentage threshold.

4. The system of claim 2 wherein said ratio selection window includes a numerical box configured to allow said user to enter said occlusion percentage threshold.

5. The system of claim 1 wherein said processor is further configured to determine a percentage of occlusion in said lumen.

6. The system of claim 5 wherein said processor is configured to take into account at least one of a plaque type and a plaque density in determining said percentage of occlusion in said lumen.

7. The system of claim 5 wherein said percentage of occlusion is determined in accordance with the following relationship:

$$\% \text{ BLOCKED} = \left(1 - \frac{S_{LUMEN}}{S_{ARTERY}}\right) \cdot 100$$

where % BLOCKED denotes said percentage of occlusion, $S_{LUMEN}$ denotes the cross-sectional area of a duct portion of said lumen and $S_{ARTERY}$ denotes a total internal cross-sectional area of said lumen.

8. The system of claim 1 wherein said processor is further configured to designate said identified region on said image with a plurality of marks corresponding to a rear end, a middle and a front end of said identified region.

9. The system of claim 8 where a distance between said rear end and front end marks corresponds to a type of stent selected for mounting in said lumen.

10. The system of claim 9 wherein said type of stent includes a size of said stent.

11. The system of claim 1 wherein said mark is differentiated from a remainder of said image of said lumen.

12. The system of claim 11 wherein said mark is differentiated by being colored in a different hue, being marked by hatches, being animated, being a different shape or being a different size.

13. The system of claim 1 wherein said stent representation comprises a front end feature corresponding to a front end of said stent and a rear end feature corresponding to a rear end of said stent.

14. The system of claim 1 wherein said user interface is further configured to allow said user to manually correct said position of said mark designating said identified region.

15. The system of claim 14 wherein said processor is configured to designate said identified region on said image with a plurality of marks corresponding to a rear end, a middle and a front end of said identified region, said user interface being configured to allow said user to move said plurality of marks together along a trajectory corresponding to said lumen, said marks being locked-on said trajectory and being operative to travel along said trajectory.

16. The system of claim 14 wherein said user interface is responsive to a user input device to effect marking, said input device being one selected from the group comprising a joystick, a push button and a pointing device including a mouse, a stylus and digital tablet, a track-ball and a touch pad.

17. The system of claim 1 wherein said processor is configured to designate said identified region on said image with a plurality of marks corresponding to a rear end, a middle and a front end of said identified region, said processor being configured to determine when a front end of said stent is substantially aligned with said front end mark and said rear end of said stent is substantially aligned with said rear end mark.

18. The system of claim 1 wherein said output comprises an announcement via one of an audio, visual or tactile device.

19. A system for delivering a stent coupled with a catheter to a selected position within a lumen of the body of a patient, comprising:

a medical positioning system (MPS) for determining a current position of said stent within said lumen, in a coordinate system respective of said MPS, according to position data acquired by an MPS sensor attached to said catheter in the vicinity of said stent;

a user interface configured to allow a user to select an occlusion percentage threshold;

a processor coupled with said user interface and with said MPS, said processor configured to determine said selected position in said lumen to which said stent is to be delivered by identifying a region of said lumen that is occluded more than said selected occlusion percentage threshold, said processor being further configured to designate said identified region on an image of said lumen with at least one mark;

wherein said user interface is further configured to allow said user to manually correct said position in said lumen of said mark that designates said identified region by allowing said user to move said mark along a trajectory corresponding to said lumen;

said MPS being further configured to repeatedly determine said current position while said catheter is being maneuvered within said lumen, said processor being configured to superimpose a stent representation respective of said determined current position on said image;

said processor being further configured to produce an output when said current position, represented by said stent representation in said image, is substantially aligned with said selected position, represented by said mark in said image.

* * * * *